US007189393B2

(12) United States Patent
Rybak et al.

(10) Patent No.: US 7,189,393 B2
(45) Date of Patent: *Mar. 13, 2007

(54) RECOMBINANT ANTI-TUMOR RNASE

(75) Inventors: Susanna M. Rybak, Green Cove Springs, FL (US); Dianne L. Newton, Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 712 days.

This patent is subject to a terminal disclaimer.

(21) Appl. No.: 09/948,391

(22) Filed: Sep. 6, 2001

(65) Prior Publication Data

US 2003/0027311 A1 Feb. 6, 2003

Related U.S. Application Data

(63) Continuation of application No. 09/622,613, filed as application No. PCT/US99/06641 on Mar. 26, 1999, now Pat. No. 6,869,604.

(60) Provisional application No. 60/079,751, filed on Mar. 27, 1998.

(51) Int. Cl.
*A61K 38/43* (2006.01)
(52) U.S. Cl. ............................. 424/94.61; 424/134.1; 435/199
(58) Field of Classification Search ............. 424/94.61, 424/134.1; 435/199
See application file for complete search history.

(56) References Cited

U.S. PATENT DOCUMENTS 5,840,840 A 11/1998 Rybak et al.
6,395,276 B1 5/2002 Rybak et al.

FOREIGN PATENT DOCUMENTS

| WO | WO 97/31116 A2 | 8/1997 |
| WO | WO 97/31116 A3 | 8/1997 |
| WO | WO 97/38112 A1 | 10/1997 |
| WO | WO 98/50435 A1 | 11/1998 |
| WO | WO 99/50398 A2 | 10/1999 |

OTHER PUBLICATIONS

Ardelt et al (1991, J. Biol. Chem. vol. 266, pp. 245-251), IDS 7.*
Newton et al (1998, Biochemistry vol. 37, pp. 5173-5183), IDS 17.*
Newton et al (1997, Protein Engineering, vol. 10, pp. 463-470), IDS 16.*
Chen et al (Nucleic Acids Res. Jun. 15, 2000: 28(12): 2375-82).*
Ardelt, W. et al. "Amino Acid Sequence of an Anti-Tumor Protein from *Rana pipiens* Oocytes and Early Embryos/ Homology to Pancreatic Ribonucleases," *J. Biol. Chem.* 1991, pp. 245-251, vol. 266, No. 1.
Boix, E. et al. "Role of the N-Terminus in RNase A Homologues: Differences in Catalytic Activity, Ribonuclease Inhibitor Interaction and Cytotoxicity," *J. Mol. Biol.* 1996, pp. 992-1007, vol. 257.
Inokuchi et al. "Primary Structures of Base Non-Specific and Acid Ribonuclease from Bullfrog (*Rana catesbeiana*)" *Biol. Pharm. Bull* 1997, pp. 471-478, vol. 20, No. 5.
Kobe et al. "A structural Basis of the Interactions Between Leucine-Rich Repeats and Protein Ligands," *Nature* 1995, pp. 183-186, vol. 374.
Leung, S.O. et al. "Recombinant Expression of Ribonuclease of *Rana pipien* Origin," *Proceedings of the 90th Annual Meeting of The American Association for Cancer Research*, Philadelphia, PA, Apr. 10-14, 1999, pp. 353-354, vol. 40 (Abstract #2341).
Liao et al. "Large-Scale Preparation of a Ribonuclease from *Rana catesbeiana* (Bullfrog) Oocytes and Characterization of its Specific Cytotoxic Activity Against Tumor Cells" *Protein Expression and Purfication* 1996, pp. 194-202, vol. 7.
Mansfield et al. "Recombinant RFB4 Immunotoxins Exhibit Potent Cytotoxic Activity for CD22-Bearing Cells and Tumors" *Blood* Sep. 1997, pp. 2020-2026, vol. 90, No. 5.
Mansfield et al. "Recombinant RFB4 Single-Chain Immunotoxin that is Cytotoxic Towards CD22-Positive Cells" *Biochem. Soc. Trans.* 1997, pp. 709-714, vol. 25.
Mosimann, S.C. et al. "Refined 1-7 Å X-Ray Crystallographic Structure of P-30 Protein, an Amphibian Ribonuclease with Anti-Tumor Activity," *J. Mol. Biol.* 1994, pp. 1141-1153, vol. 236.
Newton, D.L. et al. "Expression and Characterization of a Cytotoxic Human-Frog Chimeric Ribonuclease: Potential for Cancer Therapy," *Protein Engineering* 1997, pp. 463-470, vol. 10, No. 4.

(Continued)

Primary Examiner—Misook Yu
(74) Attorney, Agent, or Firm—Townsend and Townsend and Crew LLP

(57) ABSTRACT

This invention provides for new recombinant ribonuclease proteins which are active when expressed by bacteria. This allows the recombinant ribonucleases of this invention to be fused in-frame with ligand binding moieties to form cytotoxic fusion proteins. Furthermore, these proteins are more active than ribonucleases currently available even though the proteins of this invention lack an N-terminal pyroglutamic acid, which has been found to be necessary for ribonucleolytic activity. Because these proteins are recombinant proteins, mutations which increase cytotoxicity can be engineered.

8 Claims, No Drawings

OTHER PUBLICATIONS

Newton, D.L. et al. "Single Amino Acid Substitutions at the N-Terminus of a Recombinant Cytotoxic Ribonuclease Markedly Influence Biochemical and Biological Properties," *Biochemistry* 1998, pp. 5173-5183, vol. 37, No. 15.

Newton, D.L. et al. "Angiogenin Single-Chain Immunofusions: Influence of Peptide Linkers and Spacers Between Fusion Protein Domains" *Biochemistry* 1996, pp. 545-553, vol. 35.

Newton, D.L. et al. "Anti-Tumor Ribonuclease, Combined with or Conjugated to Monoclonal Antibody MRK16, Overcomes Multidrug Resistance to Vincristine *In Vitro* and *In Vivo*" *Int'l. Oncology* 1996, pp. 1095-1104, vol. 8.

Rybak et al. "Cytoxic Onconase and Ribonuclease A Chimeras: Comparison and *in Vitro* Characterization" *Drug Delivery* 1993, pp. 3-10, vol. 1.

* cited by examiner

SEQUENCE LISTING

```
<160> NUMBER OF SEQ ID NOS: 43

<210> SEQ ID NO 1
<211> LENGTH: 312
<212> TYPE: DNA
<213> ORGANISM: Rana pipiens
<220> FEATURE:
<221> NAME/KEY: CDS
<222> LOCATION: (1)..(312)
<223> OTHER INFORMATION: ribonuclease (RaPLR1)

<400> SEQUENCE: 1 caa gac tgg ctt acg ttt cag aag aag cac ctg aca aac acc cgg gat        48
Gln Asp Trp Leu Thr Phe Gln Lys Lys His Leu Thr Asn Thr Arg Asp
  1               5                  10                  15 gtt gac tgt aat att atc atg tca aca aac ttg ttc cac tgc aag gac        96
Val Asp Cys Asn Ile Ile Met Ser Thr Asn Leu Phe His Cys Lys Asp
             20                  25                  30 aag aac act ttt atc tat tca cgt cct gag cca gtg aag gcc atc tgt       144
Lys Asn Thr Phe Ile Tyr Ser Arg Pro Glu Pro Val Lys Ala Ile Cys
         35                  40                  45 aaa gga att ata gcc tcc aaa aat gtg tta act acc tct gag ttt tat       192
Lys Gly Ile Ile Ala Ser Lys Asn Val Leu Thr Thr Ser Glu Phe Tyr
     50                  55                  60 ctc tct gat tgc aat gta aca agc agg cct tgc aag tat aaa tta aag       240
Leu Ser Asp Cys Asn Val Thr Ser Arg Pro Cys Lys Tyr Lys Leu Lys
 65                  70                  75                  80 aaa tca act aat aca ttt tgt gta act tgt gag aat caa gct cca gta       288
Lys Ser Thr Asn Thr Phe Cys Val Thr Cys Glu Asn Gln Ala Pro Val
                 85                  90                  95 cat ttc gtg ggt gtc gga cat tgc                                        312
His Phe Val Gly Val Gly His Cys
            100

<210> SEQ ID NO 2
<211> LENGTH: 104
<212> TYPE: PRT
<213> ORGANISM: Rana pipiens
<220> FEATURE:
<223> OTHER INFORMATION: ribonuclease (RaPLR1)

<400> SEQUENCE: 2

Gln Asp Trp Leu Thr Phe Gln Lys Lys His Leu Thr Asn Thr Arg Asp
  1               5                  10                  15
```

```
Val Asp Cys Asn Ile Ile Met Ser Thr Asn Leu Phe His Cys Lys Asp
            20                  25                  30

Lys Asn Thr Phe Ile Tyr Ser Arg Pro Glu Pro Val Lys Ala Ile Cys
            35                  40                  45

Lys Gly Ile Ile Ala Ser Lys Asn Val Leu Thr Thr Ser Glu Phe Tyr
 50                      55                  60

Leu Ser Asp Cys Asn Val Thr Ser Arg Pro Cys Lys Tyr Lys Leu Lys
 65                  70                  75                  80

Lys Ser Thr Asn Thr Phe Cys Val Thr Cys Glu Asn Gln Ala Pro Val
            85                  90                  95

His Phe Val Gly Val Gly His Cys
            100

<210> SEQ ID NO 3
<211> LENGTH: 312
<212> TYPE: DNA
<213> ORGANISM: Artificial Sequence
<220> FEATURE:
<223> OTHER INFORMATION: Description of Artificial Sequence:Rana
      pipiens ribonuclease with Met23Leu substitution
      (recombinant RaPLR1 Met23Leu)
<220> FEATURE:
<221> NAME/KEY: CDS
<222> LOCATION: (1)..(312)
<223> OTHER INFORMATION: RaPLR1 Met23Leu

<400> SEQUENCE: 3 caa gac tgg ctt acg ttt cag aag aag cac ctg aca aac acc cgg gat     48
Gln Asp Trp Leu Thr Phe Gln Lys Lys His Leu Thr Asn Thr Arg Asp
  1               5                  10                  15 gtt gac tgt aat aat atc ctg tca aca aac ttg ttc cac tgc aag gac     96
Val Asp Cys Asn Asn Ile Leu Ser Thr Asn Leu Phe His Cys Lys Asp
             20                  25                  30 aag aac act ttt atc tat tca cgt cct gag cca gtg aag gcc atc tgt    144
Lys Asn Thr Phe Ile Tyr Ser Arg Pro Glu Pro Val Lys Ala Ile Cys
             35                  40                  45 aaa gga att ata gcc tcc aaa aat gtg tta act acc ttt gag ttt tat    192
Lys Gly Ile Ile Ala Ser Lys Asn Val Leu Thr Thr Phe Glu Phe Tyr
 50                      55                  60 ctc tct gat tgc aat gta aca agc agg cct tgc aag tat aaa tta aag    240
Leu Ser Asp Cys Asn Val Thr Ser Arg Pro Cys Lys Tyr Lys Leu Lys
 65                  70                  75                  80 aaa tca act aat aca ttt tgt gta act tgt gag aat caa gct cca gta    288
Lys Ser Thr Asn Thr Phe Cys Val Thr Cys Glu Asn Gln Ala Pro Val
             85                  90                  95 cat ttc gtg ggt gtc gga cat tgc                                    312
His Phe Val Gly Val Gly His Cys
            100

<210> SEQ ID NO 4
<211> LENGTH: 104
<212> TYPE: PRT
<213> ORGANISM: Artificial Sequence
<220> FEATURE:
<223> OTHER INFORMATION: Description of Artificial Sequence:Rana
      pipiens ribonuclease with Met23Leu substitution
      (recombinant RaPLR1 Met23Leu)

<400> SEQUENCE: 4

Gln Asp Trp Leu Thr Phe Gln Lys Lys His Leu Thr Asn Thr Arg Asp
  1               5                  10                  15

Val Asp Cys Asn Asn Ile Leu Ser Thr Asn Leu Phe His Cys Lys Asp
             20                  25                  30
```

```
Lys Asn Thr Phe Ile Tyr Ser Arg Pro Glu Pro Val Lys Ala Ile Cys
         35                  40                  45

Lys Gly Ile Ile Ala Ser Lys Asn Val Leu Thr Thr Phe Glu Phe Tyr
 50                  55                  60

Leu Ser Asp Cys Asn Val Thr Ser Arg Pro Cys Lys Tyr Lys Leu Lys
 65                  70                  75                  80

Lys Ser Thr Asn Thr Phe Cys Val Thr Cys Glu Asn Gln Ala Pro Val
                 85                  90                  95

His Phe Val Gly Val Gly His Cys
            100
```

<210> SEQ ID NO 5
<211> LENGTH: 315
<212> TYPE: DNA
<213> ORGANISM: Artificial Sequence
<220> FEATURE:
<223> OTHER INFORMATION: Description of Artificial Sequence:Rana
      pipiens ribonuclease with Met at position 1 (recombinant
      Met(-1) RaPLR1)
<220> FEATURE:
<221> NAME/KEY: CDS
<222> LOCATION: (1)..(315)
<223> OTHER INFORMATION: Met(-1) RaPLR1

<400> SEQUENCE: 5

```
atg caa gac tgg ctt acg ttt cag aag aag cac ctg aca aac acc cgg      48
Met Gln Asp Trp Leu Thr Phe Gln Lys Lys His Leu Thr Asn Thr Arg
 1               5                  10                  15 gat gtt gac tgt aat aat atc atg tca aca aac ttg ttc cac tgc aag      96
Asp Val Asp Cys Asn Asn Ile Met Ser Thr Asn Leu Phe His Cys Lys
                 20                  25                  30 gac aag aac act ttt atc tat tca cgt cct gag cca gtg aag gcc atc     144
Asp Lys Asn Thr Phe Ile Tyr Ser Arg Pro Glu Pro Val Lys Ala Ile
         35                  40                  45 tgt aaa gga att ata gcc tcc aaa aat gtg tta act acc tct gag ttt     192
Cys Lys Gly Ile Ile Ala Ser Lys Asn Val Leu Thr Thr Ser Glu Phe
 50                  55                  60 tat ctc tct gat tgc aat gta aca agc agg cct tgc aag tat aaa tta     240
Tyr Leu Ser Asp Cys Asn Val Thr Ser Arg Pro Cys Lys Tyr Lys Leu
 65                  70                  75                  80 aag aaa tca act aat aca ttt tgt gta act tgt gag aat caa gct cca     288
Lys Lys Ser Thr Asn Thr Phe Cys Val Thr Cys Glu Asn Gln Ala Pro
                 85                  90                  95 gta cat ttc gtg ggt gtc gga cat tgc                                 315
Val His Phe Val Gly Val Gly His Cys
            100                 105
```

<210> SEQ ID NO 6
<211> LENGTH: 105
<212> TYPE: PRT
<213> ORGANISM: Artificial Sequence
<220> FEATURE:
<223> OTHER INFORMATION: Description of Artificial Sequence:Rana
      pipiens ribonuclease with Met at position 1 (recombinant
      Met(-1) RaPLR1)

<400> SEQUENCE: 6

```
Met Gln Asp Trp Leu Thr Phe Gln Lys Lys His Leu Thr Asn Thr Arg
 1               5                  10                  15

Asp Val Asp Cys Asn Asn Ile Met Ser Thr Asn Leu Phe His Cys Lys
                 20                  25                  30

Asp Lys Asn Thr Phe Ile Tyr Ser Arg Pro Glu Pro Val Lys Ala Ile
```

-continued

```
                    35                  40                  45
Cys Lys Gly Ile Ile Ala Ser Lys Asn Val Leu Thr Thr Ser Glu Phe
         50                  55                  60

Tyr Leu Ser Asp Cys Asn Val Thr Ser Arg Pro Cys Lys Tyr Lys Leu
 65                  70                  75                  80

Lys Lys Ser Thr Asn Thr Phe Cys Val Thr Cys Glu Asn Gln Ala Pro
                 85                  90                  95

Val His Phe Val Gly Val Gly His Cys
            100                 105
```

<210> SEQ ID NO 7
<211> LENGTH: 315
<212> TYPE: DNA
<213> ORGANISM: Artificial Sequence
<220> FEATURE:
<223> OTHER INFORMATION: Description of Artificial Sequence:Rana
      pipiens ribonuclease with Met at position 1 and Met24Leu
      substitution (recombinant Met(-1) RaPLR1 Met23Leu)
<220> FEATURE:
<221> NAME/KEY: CDS
<222> LOCATION: (1)..(315)
<223> OTHER INFORMATION: Met(-1) RaPLR1 Met23Leu

<400> SEQUENCE: 7

```
atg caa gac tgg ctt acg ttt cag aag aag cac ctg aca aac acc cgg        48
Met Gln Asp Trp Leu Thr Phe Gln Lys Lys His Leu Thr Asn Thr Arg
 1               5                  10                  15 gat gtt gac tgt aat aat atc ctg tca aca aac ttg ttc cac tgc aag        96
Asp Val Asp Cys Asn Asn Ile Leu Ser Thr Asn Leu Phe His Cys Lys
             20                  25                  30 gac aag aac act ttt atc tat tca cgt cct gag cca gtg aag gcc atc       144
Asp Lys Asn Thr Phe Ile Tyr Ser Arg Pro Glu Pro Val Lys Ala Ile
         35                  40                  45 tgt aaa gga att ata gcc tcc aaa aat gtg tta act acc ttt gag ttt       192
Cys Lys Gly Ile Ile Ala Ser Lys Asn Val Leu Thr Thr Phe Glu Phe
     50                  55                  60 tat ctc tct gat tgc aat gta aca agc agg cct tgc aag tat aaa tta       240
Tyr Leu Ser Asp Cys Asn Val Thr Ser Arg Pro Cys Lys Tyr Lys Leu
 65                  70                  75                  80 aag aaa tca act att aca ttt tgt gta act tgt gag aat caa gct cca       288
Lys Lys Ser Thr Ile Thr Phe Cys Val Thr Cys Glu Asn Gln Ala Pro
                 85                  90                  95 gta cat ttc gtg ggt gtc gga cat tgc                                   315
Val His Phe Val Gly Val Gly His Cys
            100                 105
```

<210> SEQ ID NO 8
<211> LENGTH: 105
<212> TYPE: PRT
<213> ORGANISM: Artificial Sequence
<220> FEATURE:
<223> OTHER INFORMATION: Description of Artificial Sequence:Rana
      pipiens ribonuclease with Met at position 1 and Met24Leu
      substitution (recombinant Met(-1) RaPLR1 Met23Leu)

<400> SEQUENCE: 8

```
Met Gln Asp Trp Leu Thr Phe Gln Lys Lys His Leu Thr Asn Thr Arg
 1               5                  10                  15

Asp Val Asp Cys Asn Asn Ile Leu Ser Thr Asn Leu Phe His Cys Lys
             20                  25                  30

Asp Lys Asn Thr Phe Ile Tyr Ser Arg Pro Glu Pro Val Lys Ala Ile
         35                  40                  45
```

-continued

```
Cys Lys Gly Ile Ile Ala Ser Lys Asn Val Leu Thr Thr Phe Glu Phe
         50                  55                  60

Tyr Leu Ser Asp Cys Asn Val Thr Ser Arg Pro Cys Lys Tyr Lys Leu
 65                  70                  75                  80

Lys Lys Ser Thr Ile Thr Phe Cys Val Thr Cys Glu Asn Gln Ala Pro
                 85                  90                  95

Val His Phe Val Gly Val Gly His Cys
            100                 105
```

<210> SEQ ID NO 9
<211> LENGTH: 111
<212> TYPE: PRT
<213> ORGANISM: Artificial Sequence
<220> FEATURE:
<223> OTHER INFORMATION: Description of Artificial Sequence:Rana
    pipiens ribonuclease with (His)6 tag, Met at position 7
    and Met30Leu substitution (recombinant Met(-1)
    RaPLR1 Met23Leu-(His)6)

<400> SEQUENCE: 9

```
His His His His His His Met Gln Asp Trp Leu Thr Phe Gln Lys Lys
  1               5                  10                  15

His Leu Thr Asn Thr Arg Asp Val Asp Cys Asn Asn Ile Leu Ser Thr
                 20                  25                  30

Asn Leu Phe His Cys Lys Asp Lys Asn Thr Phe Ile Tyr Ser Arg Pro
             35                  40                  45

Glu Pro Val Lys Ala Ile Cys Lys Gly Ile Ile Ala Ser Lys Asn Val
 50                  55                  60

Leu Thr Thr Phe Glu Phe Tyr Leu Ser Asp Cys Asn Val Thr Ser Arg
 65                  70                  75                  80

Pro Cys Lys Tyr Lys Leu Lys Lys Ser Thr Ile Thr Phe Cys Val Thr
                 85                  90                  95

Cys Glu Asn Gln Ala Pro Val His Phe Val Gly Val Gly His Cys
            100                 105                 110
```

<210> SEQ ID NO 10
<211> LENGTH: 312
<212> TYPE: DNA
<213> ORGANISM: Artificial Sequence
<220> FEATURE:
<223> OTHER INFORMATION: Description of Artificial Sequence:Rana
    pipiens ribonuclease with Gln1Ser substitution
    (recombinant RaPLR1 Q1S)
<220> FEATURE:
<221> NAME/KEY: CDS
<222> LOCATION: (1)..(312)
<223> OTHER INFORMATION: RaPLR1 Q1S

<400> SEQUENCE: 10

```
tca gac tgg ctt acg ttt cag aag aag cac ctg aca aac acc cgg gat      48
Ser Asp Trp Leu Thr Phe Gln Lys Lys His Leu Thr Asn Thr Arg Asp
  1               5                  10                  15 gtt gac tgt aat aat atc atg tca aca aac ttg ttc cac tgc aag gac      96
Val Asp Cys Asn Asn Ile Met Ser Thr Asn Leu Phe His Cys Lys Asp
             20                  25                  30 aag aac act ttt atc tat tca cgt cct gag cca gtg aag gcc atc tgt     144
Lys Asn Thr Phe Ile Tyr Ser Arg Pro Glu Pro Val Lys Ala Ile Cys
         35                  40                  45 aaa gga att ata gcc tcc aaa aat gtg tta act acc tct gag ttt tat     192
Lys Gly Ile Ile Ala Ser Lys Asn Val Leu Thr Thr Ser Glu Phe Tyr
 50                  55                  60 ctc tct gat tgc aat gta aca agc agg cct tgc aag tat aaa tta aag     240
```

-continued

```
Leu Ser Asp Cys Asn Val Thr Ser Arg Pro Cys Lys Tyr Lys Leu Lys
 65                  70                  75                  80 aaa tca act aat aca ttt tgt gta act tgt gag aat caa gct cca gta    288
Lys Ser Thr Asn Thr Phe Cys Val Thr Cys Glu Asn Gln Ala Pro Val
                 85                  90                  95 cat ttc gtg ggt gtc gga cat tgc                                    312
His Phe Val Gly Val Gly His Cys
            100
```

<210> SEQ ID NO 11
<211> LENGTH: 104
<212> TYPE: PRT
<213> ORGANISM: Artificial Sequence
<220> FEATURE:
<223> OTHER INFORMATION: Description of Artificial Sequence:Rana
      pipiens ribonuclease with Gln1Ser substitution
      (recombinant RaPLR1 Q1S)

<400> SEQUENCE: 11

```
Ser Asp Trp Leu Thr Phe Gln Lys Lys His Leu Thr Asn Thr Arg Asp
 1               5                  10                  15

Val Asp Cys Asn Asn Ile Met Ser Thr Asn Leu Phe His Cys Lys Asp
                20                  25                  30

Lys Asn Thr Phe Ile Tyr Ser Arg Pro Glu Pro Val Lys Ala Ile Cys
             35                  40                  45

Lys Gly Ile Ile Ala Ser Lys Asn Val Leu Thr Thr Ser Glu Phe Tyr
         50                  55                  60

Leu Ser Asp Cys Asn Val Thr Ser Arg Pro Cys Lys Tyr Lys Leu Lys
 65                  70                  75                  80

Lys Ser Thr Asn Thr Phe Cys Val Thr Cys Glu Asn Gln Ala Pro Val
                 85                  90                  95

His Phe Val Gly Val Gly His Cys
            100
```

<210> SEQ ID NO 12
<211> LENGTH: 315
<212> TYPE: DNA
<213> ORGANISM: Artificial Sequence
<220> FEATURE:
<223> OTHER INFORMATION: Description of Artificial Sequence:Rana
      pipiens ribonuclease with Met at position 1 and Gln2Ser
      substitution (recombinant Met(-1) RaPLR1 Q1S)
<220> FEATURE:
<221> NAME/KEY: CDS
<222> LOCATION: (1)..(315)
<223> OTHER INFORMATION: Met(-1) RaPLR1 Q1S

<400> SEQUENCE: 12

```
atg tca gac tgg ctt acg ttt cag aag aag cac ctg aca aac acc cgg    48
Met Ser Asp Trp Leu Thr Phe Gln Lys Lys His Leu Thr Asn Thr Arg
 1               5                  10                  15 gat gtt gac tgt aat aat atc atg tca aca aac ttg ttc cac tgc aag    96
Asp Val Asp Cys Asn Asn Ile Met Ser Thr Asn Leu Phe His Cys Lys
                20                  25                  30 gac aag aac act ttt atc tat tca cgt cct gag cca gtg aag gcc atc   144
Asp Lys Asn Thr Phe Ile Tyr Ser Arg Pro Glu Pro Val Lys Ala Ile
             35                  40                  45 tgt aaa gga att ata gcc tcc aaa aat gtg tta act acc tct gag ttt   192
Cys Lys Gly Ile Ile Ala Ser Lys Asn Val Leu Thr Thr Ser Glu Phe
         50                  55                  60 tat ctc tct gat tgc aat gta aca agc agg cct tgc aag tat aaa tta   240
Tyr Leu Ser Asp Cys Asn Val Thr Ser Arg Pro Cys Lys Tyr Lys Leu
 65                  70                  75                  80
```

```
aag aaa tca act aat aca ttt tgt gta act tgt gag aat caa gct cca        288
Lys Lys Ser Thr Asn Thr Phe Cys Val Thr Cys Glu Asn Gln Ala Pro
                85                  90                  95 gta cat ttc gtg ggt gtc gga cat tgc                                    315
Val His Phe Val Gly Val Gly His Cys
            100                 105
```

<210> SEQ ID NO 13
<211> LENGTH: 105
<212> TYPE: PRT
<213> ORGANISM: Artificial Sequence
<220> FEATURE:
<223> OTHER INFORMATION: Description of Artificial Sequence:Rana
      pipiens ribonuclease with Met at position 1 and Gln2Ser
      substitution (recombinant Met(-1) RaPLR1 Q1S)

<400> SEQUENCE: 13

```
Met Ser Asp Trp Leu Thr Phe Gln Lys Lys His Leu Thr Asn Thr Arg
 1               5                  10                  15

Asp Val Asp Cys Asn Asn Ile Met Ser Thr Asn Leu Phe His Cys Lys
                20                  25                  30

Asp Lys Asn Thr Phe Ile Tyr Ser Arg Pro Glu Pro Val Lys Ala Ile
            35                  40                  45

Cys Lys Gly Ile Ile Ala Ser Lys Asn Val Leu Thr Thr Ser Glu Phe
    50                  55                  60

Tyr Leu Ser Asp Cys Asn Val Thr Ser Arg Pro Cys Lys Tyr Lys Leu
 65                 70                  75                  80

Lys Lys Ser Thr Asn Thr Phe Cys Val Thr Cys Glu Asn Gln Ala Pro
                85                  90                  95

Val His Phe Val Gly Val Gly His Cys
            100                 105
```

<210> SEQ ID NO 14
<211> LENGTH: 330
<212> TYPE: DNA
<213> ORGANISM: Artificial Sequence
<220> FEATURE:
<223> OTHER INFORMATION: Description of Artificial Sequence:Rana
      catesbeiana oocyte ribonuclease (RaCOR1) synthetic
      gene modified to use E. coli preferred codons
<220> FEATURE:
<221> NAME/KEY: CDS
<222> LOCATION: (1)..(330)
<223> OTHER INFORMATION: RaCOR1 for E. coli expression system

<400> SEQUENCE: 14

```
cag aac tgg gct act ttc cag cag aaa cat atc atc aac act ccg atc        48
Gln Asn Trp Ala Thr Phe Gln Gln Lys His Ile Ile Asn Thr Pro Ile
 1               5                  10                  15 atc tgc aac act atc atg gac aac aac atc tac atc gtt ggt ggt cag        96
Ile Cys Asn Thr Ile Met Asp Asn Asn Ile Tyr Ile Val Gly Gly Gln
                20                  25                  30 tgc aaa cgt gtt aac act ttc atc atc tct tct gct act act gtt aaa       144
Cys Lys Arg Val Asn Thr Phe Ile Ile Ser Ser Ala Thr Thr Val Lys
            35                  40                  45 gct atc tgc act ggt gtt atc aac atg aac gtt ctg tct act act cgt       192
Ala Ile Cys Thr Gly Val Ile Asn Met Asn Val Leu Ser Thr Thr Arg
    50                  55                  60 ttc cag ctg aac act tgc act cgt act tct atc act ccg cgt ccg tgc       240
Phe Gln Leu Asn Thr Cys Thr Arg Thr Ser Ile Thr Pro Arg Pro Cys
 65                 70                  75                  80 ccg tac tct tct cgt act gaa act aac tac atc tgc gtt aaa tgc gaa       288
Pro Tyr Ser Ser Arg Thr Glu Thr Asn Tyr Ile Cys Val Lys Cys Glu
```

```
Pro Tyr Ser Ser Arg Thr Glu Thr Asn Tyr Ile Cys Val Lys Cys Glu
            85                  90                  95 aac cag tac ccg gtt cat ttc gct ggt atc ggt cgt tgc ccg          330
Asn Gln Tyr Pro Val His Phe Ala Gly Ile Gly Arg Cys Pro
            100                 105                 110

<210> SEQ ID NO 15
<211> LENGTH: 110
<212> TYPE: PRT
<213> ORGANISM: Artificial Sequence
<220> FEATURE:
<223> OTHER INFORMATION: Description of Artificial Sequence:Rana
      catesbeiana oocyte ribonuclease (RaCOR1) synthetic
      gene modified to use E. coli preferred codons

<400> SEQUENCE: 15

Gln Asn Trp Ala Thr Phe Gln Gln Lys His Ile Ile Asn Thr Pro Ile
 1               5                  10                  15

Ile Cys Asn Thr Ile Met Asp Asn Asn Ile Tyr Ile Val Gly Gly Gln
            20                  25                  30

Cys Lys Arg Val Asn Thr Phe Ile Ile Ser Ser Ala Thr Thr Val Lys
        35                  40                  45

Ala Ile Cys Thr Gly Val Ile Asn Met Asn Val Leu Ser Thr Thr Arg
    50                  55                  60

Phe Gln Leu Asn Thr Cys Thr Arg Thr Ser Ile Thr Pro Arg Pro Cys
65                  70                  75                  80

Pro Tyr Ser Ser Arg Thr Glu Thr Asn Tyr Ile Cys Val Lys Cys Glu
            85                  90                  95

Asn Gln Tyr Pro Val His Phe Ala Gly Ile Gly Arg Cys Pro
            100                 105                 110

<210> SEQ ID NO 16
<211> LENGTH: 333
<212> TYPE: DNA
<213> ORGANISM: Artificial Sequence
<220> FEATURE:
<223> OTHER INFORMATION: Description of Artificial Sequence:Rana
      catesbeiana ribonuclease with Met at position 1
      (recombinant Met(-1) RaCOR1)
<220> FEATURE:
<221> NAME/KEY: CDS
<222> LOCATION: (1)..(333)
<223> OTHER INFORMATION: Met(-1) RaCOR1

<400> SEQUENCE: 16 atg cag aac tgg gct act ttc cag cag aaa cat atc atc aac act ccg   48
Met Gln Asn Trp Ala Thr Phe Gln Gln Lys His Ile Ile Asn Thr Pro
 1               5                  10                  15 atc atc tgc aac act atc atg gac aac aac atc tac atc gtt ggt ggt   96
Ile Ile Cys Asn Thr Ile Met Asp Asn Asn Ile Tyr Ile Val Gly Gly
            20                  25                  30 cag tgc aaa cgt gtt acc act ttc atc atc tct tct gct act act gtt  144
Gln Cys Lys Arg Val Thr Thr Phe Ile Ile Ser Ser Ala Thr Thr Val
        35                  40                  45 aaa gct atc tgc act ggt gtt atc aac atg aac gtt ctg tct act act  192
Lys Ala Ile Cys Thr Gly Val Ile Asn Met Asn Val Leu Ser Thr Thr
    50                  55                  60 cgt ttc cag ctg aac act tgc act cgt act tct atc act ccg cgt ccg  240
Arg Phe Gln Leu Asn Thr Cys Thr Arg Thr Ser Ile Thr Pro Arg Pro
65                  70                  75                  80 tgc ccg tac tct tct cgt act gaa act aac tac atc tgc gtt aaa tgc  288
Cys Pro Tyr Ser Ser Arg Thr Glu Thr Asn Tyr Ile Cys Val Lys Cys
            85                  90                  95
```

```
gaa aac cag tac ccg gtt cat ttc gct ggt atc ggt cgt tgc ccg        333
Glu Asn Gln Tyr Pro Val His Phe Ala Gly Ile Gly Arg Cys Pro
            100                 105                 110

<210> SEQ ID NO 17
<211> LENGTH: 111
<212> TYPE: PRT
<213> ORGANISM: Artificial Sequence
<220> FEATURE:
<223> OTHER INFORMATION: Description of Artificial Sequence:Rana
      catesbeiana ribonuclease with Met at position 1
      (recombinant Met(-1) RaCOR1)

<400> SEQUENCE: 17

Met Gln Asn Trp Ala Thr Phe Gln Gln Lys His Ile Ile Asn Thr Pro
 1               5                  10                  15

Ile Ile Cys Asn Thr Ile Met Asp Asn Asn Ile Tyr Ile Val Gly Gly
                20                  25                  30

Gln Cys Lys Arg Val Thr Thr Phe Ile Ile Ser Ser Ala Thr Thr Val
            35                  40                  45

Lys Ala Ile Cys Thr Gly Val Ile Asn Met Asn Val Leu Ser Thr Thr
 50                  55                  60

Arg Phe Gln Leu Asn Thr Cys Thr Arg Thr Ser Ile Thr Pro Arg Pro
 65                  70                  75                  80

Cys Pro Tyr Ser Ser Arg Thr Glu Thr Asn Tyr Ile Cys Val Lys Cys
                85                  90                  95

Glu Asn Gln Tyr Pro Val His Phe Ala Gly Ile Gly Arg Cys Pro
            100                 105                 110

<210> SEQ ID NO 18
<211> LENGTH: 330
<212> TYPE: DNA
<213> ORGANISM: Artificial Sequence
<220> FEATURE:
<223> OTHER INFORMATION: Description of Artificial Sequence:Rana
      catesbeiana ribonuclease with Met22Leu and
      Met57Leu substitutions (recombinant RaCOR1
      Met22Leu Met57Leu)
<220> FEATURE:
<221> NAME/KEY: CDS
<222> LOCATION: (1)..(330)
<223> OTHER INFORMATION: RaCOR1 Met22Leu Met57Leu

<400> SEQUENCE: 18 cag aac tgg gct act ttc cag cag aaa cat atc atc aaa act ccg atc    48
Gln Asn Trp Ala Thr Phe Gln Gln Lys His Ile Ile Lys Thr Pro Ile
 1               5                  10                  15 atc tgc aac act atc ctg gac aac aac atc tac atc gtt ggt ggt cag    96
Ile Cys Asn Thr Ile Leu Asp Asn Asn Ile Tyr Ile Val Gly Gly Gln
                20                  25                  30 tgc aaa cgt gtt aac act ttc atc atc tct tct gct act act gtt aaa   144
Cys Lys Arg Val Asn Thr Phe Ile Ile Ser Ser Ala Thr Thr Val Lys
            35                  40                  45 gct atc tgc act ggt gtt atc aac ctg aac gtt ctg tct act act cgt   192
Ala Ile Cys Thr Gly Val Ile Asn Leu Asn Val Leu Ser Thr Thr Arg
 50                  55                  60 ttc cag ctg aac act tgc act cgt act tct atc act ccg cgt ccg tgc   240
Phe Gln Leu Asn Thr Cys Thr Arg Thr Ser Ile Thr Pro Arg Pro Cys
 65                  70                  75                  80 ccg tac tct tct cgt act gaa act aac tac atc tgc gtt aaa tgc gaa   288
Pro Tyr Ser Ser Arg Thr Glu Thr Asn Tyr Ile Cys Val Lys Cys Glu
                85                  90                  95
```

```
aac cag tac ccg gtt cat ttc gct ggt atc ggt cgt tgc ccg          330
Asn Gln Tyr Pro Val His Phe Ala Gly Ile Gly Arg Cys Pro
            100                 105                 110

<210> SEQ ID NO 19
<211> LENGTH: 110
<212> TYPE: PRT
<213> ORGANISM: Artificial Sequence
<220> FEATURE:
<223> OTHER INFORMATION: Description of Artificial Sequence:Rana
      catesbeiana ribonuclease with Met22Leu and
      Met57Leu substitutions (recombinant RaCOR1
      Met22Leu Met57Leu)

<400> SEQUENCE: 19

Gln Asn Trp Ala Thr Phe Gln Gln Lys His Ile Ile Lys Thr Pro Ile
 1               5                  10                  15

Ile Cys Asn Thr Ile Leu Asp Asn Asn Ile Tyr Ile Val Gly Gly Gln
            20                  25                  30

Cys Lys Arg Val Asn Thr Phe Ile Ile Ser Ser Ala Thr Thr Val Lys
        35                  40                  45

Ala Ile Cys Thr Gly Val Ile Asn Leu Asn Val Leu Ser Thr Thr Arg
    50                  55                  60

Phe Gln Leu Asn Thr Cys Thr Arg Thr Ser Ile Thr Pro Arg Pro Cys
65                  70                  75                  80

Pro Tyr Ser Ser Arg Thr Glu Thr Asn Tyr Ile Cys Val Lys Cys Glu
                85                  90                  95

Asn Gln Tyr Pro Val His Phe Ala Gly Ile Gly Arg Cys Pro
            100                 105                 110

<210> SEQ ID NO 20
<211> LENGTH: 333
<212> TYPE: DNA
<213> ORGANISM: Artificial Sequence
<220> FEATURE:
<223> OTHER INFORMATION: Description of Artificial Sequence:Rana
      catesbeiana ribonuclease with Met at position 1,
      Met23Leu and Met58Leu substitutions (recombinant
      Met(-1) RaCOR1 Met22Leu Met57Leu)
<220> FEATURE:
<221> NAME/KEY: CDS
<222> LOCATION: (1)..(333)
<223> OTHER INFORMATION: Met(-1) RaCOR1 Met22Leu Met57Leu

<400> SEQUENCE: 20 atg cag aac tgg gct act ttc cag cag aaa cat atc atc aac act ccg          48
Met Gln Asn Trp Ala Thr Phe Gln Gln Lys His Ile Ile Asn Thr Pro
 1               5                  10                  15 atc atc tgc aac act atc ctg gac aac aac atc tac atc gtt ggt ggt          96
Ile Ile Cys Asn Thr Ile Leu Asp Asn Asn Ile Tyr Ile Val Gly Gly
            20                  25                  30 cag tgc aaa cgt gtt aac act ttc atc atc tct tct gct act act gtt         144
Gln Cys Lys Arg Val Asn Thr Phe Ile Ile Ser Ser Ala Thr Thr Val
        35                  40                  45 aaa gct atc tgc act ggt gtt atc aac ctg aac gtt ctg tct act act         192
Lys Ala Ile Cys Thr Gly Val Ile Asn Leu Asn Val Leu Ser Thr Thr
    50                  55                  60 cgt ttc cag ctg aac act tgc act cgt act tct atc act ccg cgt ccg         240
Arg Phe Gln Leu Asn Thr Cys Thr Arg Thr Ser Ile Thr Pro Arg Pro
65                  70                  75                  80 tgc ccg tac tct tct cgt act gaa act aac tac atc tgc gtt aaa tgc         288
Cys Pro Tyr Ser Ser Arg Thr Glu Thr Asn Tyr Ile Cys Val Lys Cys
                85                  90                  95
```

```
gaa aac cag tac ccg gtt cat ttc gct ggt atc ggt cgt tgc ccg        333
Glu Asn Gln Tyr Pro Val His Phe Ala Gly Ile Gly Arg Cys Pro
100                 105                 110
```

<210> SEQ ID NO 21
<211> LENGTH: 111
<212> TYPE: PRT
<213> ORGANISM: Artificial Sequence
<220> FEATURE:
<223> OTHER INFORMATION: Description of Artificial Sequence:Rana
      catesbeiana ribonuclease with Met at position 1,
      Met23Leu and Met58Leu substitutions (recombinant
      Met(-1) RaCOR1 Met22Leu Met57Leu)

<400> SEQUENCE: 21

```
Met Gln Asn Trp Ala Thr Phe Gln Gln Lys His Ile Ile Asn Thr Pro
1               5                   10                  15

Ile Ile Cys Asn Thr Ile Leu Asp Asn Asn Ile Tyr Ile Val Gly Gly
            20                  25                  30

Gln Cys Lys Arg Val Asn Thr Phe Ile Ile Ser Ser Ala Thr Thr Val
        35                  40                  45

Lys Ala Ile Cys Thr Gly Val Ile Asn Leu Asn Val Leu Ser Thr Thr
    50                  55                  60

Arg Phe Gln Leu Asn Thr Cys Thr Arg Thr Ser Ile Thr Pro Arg Pro
65                  70                  75                  80

Cys Pro Tyr Ser Ser Arg Thr Glu Thr Asn Tyr Ile Cys Val Lys Cys
                85                  90                  95

Glu Asn Gln Tyr Pro Val His Phe Ala Gly Ile Gly Arg Cys Pro
            100                 105                 110
```

<210> SEQ ID NO 22
<211> LENGTH: 117
<212> TYPE: PRT
<213> ORGANISM: Artificial Sequence
<220> FEATURE:
<223> OTHER INFORMATION: Description of Artificial Sequence:Rana
      catesbeiana ribonuclease with (His)6 tag, Met at
      position 7, Met23Leu and Met58Leu substitutions
      (recombinant Met(-1) RaCOR1 Met22Leu Met57Leu-(His)6)

<400> SEQUENCE: 22

```
His His His His His His Met Gln Asn Trp Ala Thr Phe Gln Gln Lys
1               5                   10                  15

His Ile Ile Asn Thr Pro Ile Ile Cys Asn Thr Ile Leu Asp Asn Asn
            20                  25                  30

Ile Tyr Ile Val Gly Gly Gln Cys Lys Arg Val Asn Thr Phe Ile Ile
        35                  40                  45

Ser Ser Ala Thr Thr Val Lys Ala Ile Cys Thr Gly Val Ile Asn Leu
    50                  55                  60

Asn Val Leu Ser Thr Thr Arg Phe Gln Leu Asn Thr Cys Thr Arg Thr
65                  70                  75                  80

Ser Ile Thr Pro Arg Pro Cys Pro Tyr Ser Ser Arg Thr Glu Thr Asn
                85                  90                  95

Tyr Ile Cys Val Lys Cys Glu Asn Gln Tyr Pro Val His Phe Ala Gly
            100                 105                 110

Ile Gly Arg Cys Pro
        115
```

<210> SEQ ID NO 23
<211> LENGTH: 330
<212> TYPE: DNA

-continued

```
<213> ORGANISM: Artificial Sequence
<220> FEATURE:
<223> OTHER INFORMATION: Description of Artificial Sequence:Rana
      catesbeiana ribonuclease with Gln1Ser substitution
      (recombinant RaCOR1 Q1S)
<220> FEATURE:
<221> NAME/KEY: CDS
<222> LOCATION: (1)..(330)
<223> OTHER INFORMATION: RaCOR1 Q1S

<400> SEQUENCE: 23 tca aac tgg gct act ttc cag cag aaa cat atc atc aac act ccg atc      48
Ser Asn Trp Ala Thr Phe Gln Gln Lys His Ile Ile Asn Thr Pro Ile
 1               5                  10                  15 atc tgc aac act atc atg gac aac aac atc tac atc gtt ggt ggt cag      96
Ile Cys Asn Thr Ile Met Asp Asn Asn Ile Tyr Ile Val Gly Gly Gln
            20                  25                  30 tgc aaa cgt gtt aac act ttc atc atc tct tct gct act act gtt aaa     144
Cys Lys Arg Val Asn Thr Phe Ile Ile Ser Ser Ala Thr Thr Val Lys
        35                  40                  45 gct atc tgc act ggt gtt atc aac atg aac gtt ctg tct act act cgt     192
Ala Ile Cys Thr Gly Val Ile Asn Met Asn Val Leu Ser Thr Thr Arg
    50                  55                  60 ttc cag ctg aac act tgc act cgt act tct atc act ccg cgt ccg tgc     240
Phe Gln Leu Asn Thr Cys Thr Arg Thr Ser Ile Thr Pro Arg Pro Cys
65                  70                  75                  80 ccg tac tct tct cgt act gaa act aac tac atc tgc gtt aaa tgc gaa     288
Pro Tyr Ser Ser Arg Thr Glu Thr Asn Tyr Ile Cys Val Lys Cys Glu
                85                  90                  95 aac cag tac ccg gtt cat ttc gct ggt atc ggt cgt tgc ccg             330
Asn Gln Tyr Pro Val His Phe Ala Gly Ile Gly Arg Cys Pro
            100                 105                 110

<210> SEQ ID NO 24
<211> LENGTH: 110
<212> TYPE: PRT
<213> ORGANISM: Artificial Sequence
<220> FEATURE:
<223> OTHER INFORMATION: Description of Artificial Sequence:Rana
      catesbeiana ribonuclease with Gln1Ser substitution
      (recombinant RaCOR1 Q1S)

<400> SEQUENCE: 24

Ser Asn Trp Ala Thr Phe Gln Gln Lys His Ile Ile Asn Thr Pro Ile
 1               5                  10                  15

Ile Cys Asn Thr Ile Met Asp Asn Asn Ile Tyr Ile Val Gly Gly Gln
            20                  25                  30

Cys Lys Arg Val Asn Thr Phe Ile Ile Ser Ser Ala Thr Thr Val Lys
        35                  40                  45

Ala Ile Cys Thr Gly Val Ile Asn Met Asn Val Leu Ser Thr Thr Arg
    50                  55                  60

Phe Gln Leu Asn Thr Cys Thr Arg Thr Ser Ile Thr Pro Arg Pro Cys
65                  70                  75                  80

Pro Tyr Ser Ser Arg Thr Glu Thr Asn Tyr Ile Cys Val Lys Cys Glu
                85                  90                  95

Asn Gln Tyr Pro Val His Phe Ala Gly Ile Gly Arg Cys Pro
            100                 105                 110

<210> SEQ ID NO 25
<211> LENGTH: 333
<212> TYPE: DNA
<213> ORGANISM: Artificial Sequence
<220> FEATURE:
```

-continued

<223> OTHER INFORMATION: Description of Artificial Sequence:Rana
      catesbeiana ribonuclease with Met at position 1
      and Gln2Ser substitution (Met(-1) RaCOR1 Q1S)
<220> FEATURE:
<221> NAME/KEY: CDS
<222> LOCATION: ()..(333)
<223> OTHER INFORMATION: Met(-1) RaCOR1 Q1S

<400> SEQUENCE: 25

```
atg tca aac tgg gct act ttc cag cag aaa cat atc atc aac act ccg      48
Met Ser Asn Trp Ala Thr Phe Gln Gln Lys His Ile Ile Asn Thr Pro
 1               5                  10                  15 atc atc tgc aac act atc atg gac aac aac atc tac atc gtt ggt ggt      96
Ile Ile Cys Asn Thr Ile Met Asp Asn Asn Ile Tyr Ile Val Gly Gly
             20                  25                  30 cag tgc aaa cgt gtt aac act ttc atc atc tct tct gct act act gtt     144
Gln Cys Lys Arg Val Asn Thr Phe Ile Ile Ser Ser Ala Thr Thr Val
         35                  40                  45 aaa gct atc tgc act ggt gtt atc aac atg aac gtt ctg tct act act     192
Lys Ala Ile Cys Thr Gly Val Ile Asn Met Asn Val Leu Ser Thr Thr
 50                  55                  60 cgt ttc cag ctg aac act tgc act cgt act tct atc act ccg cgt ccg     240
Arg Phe Gln Leu Asn Thr Cys Thr Arg Thr Ser Ile Thr Pro Arg Pro
 65                  70                  75                  80 tgc ccg tac tct tct cgt act gaa act aac tac atc tgc gtt aaa tgc     288
Cys Pro Tyr Ser Ser Arg Thr Glu Thr Asn Tyr Ile Cys Val Lys Cys
                 85                  90                  95 gaa aac cag tac ccg gtt cat ttc gct ggt atc ggt cgt tgc ccg         333
Glu Asn Gln Tyr Pro Val His Phe Ala Gly Ile Gly Arg Cys Pro
            100                 105                 110
```

<210> SEQ ID NO 26
<211> LENGTH: 111
<212> TYPE: PRT
<213> ORGANISM: Artificial Sequence
<220> FEATURE:
<223> OTHER INFORMATION: Description of Artificial Sequence:Rana
      catesbeiana ribonuclease with Met at position 1
      and Gln2Ser substitution (Met(-1) RaCOR1 Q1S)

<400> SEQUENCE: 26

```
Met Ser Asn Trp Ala Thr Phe Gln Gln Lys His Ile Ile Asn Thr Pro
 1               5                  10                  15

Ile Ile Cys Asn Thr Ile Met Asp Asn Asn Ile Tyr Ile Val Gly Gly
             20                  25                  30

Gln Cys Lys Arg Val Asn Thr Phe Ile Ile Ser Ser Ala Thr Thr Val
         35                  40                  45

Lys Ala Ile Cys Thr Gly Val Ile Asn Met Asn Val Leu Ser Thr Thr
 50                  55                  60

Arg Phe Gln Leu Asn Thr Cys Thr Arg Thr Ser Ile Thr Pro Arg Pro
 65                  70                  75                  80

Cys Pro Tyr Ser Ser Arg Thr Glu Thr Asn Tyr Ile Cys Val Lys Cys
                 85                  90                  95

Glu Asn Gln Tyr Pro Val His Phe Ala Gly Ile Gly Arg Cys Pro
            100                 105                 110
```

<210> SEQ ID NO 27
<211> LENGTH: 2855
<212> TYPE: DNA
<213> ORGANISM: Rana pipiens
<220> FEATURE:
<223> OTHER INFORMATION: Rana pipiens ribonuclease (RaPLR1) Clone
      5a1b cDNA insert

```
<220> FEATURE:
<221> NAME/KEY: CDS
<222> LOCATION: (97)..(481)
<223> OTHER INFORMATION: RaPLR1
<220> FEATURE:
<221> NAME/KEY: sig_peptide
<222> LOCATION: (97)..(165)

<400> SEQUENCE: 27
atcagttgct catcgtttga ccaagttgtt ttccatctga agcaatattt atatataatt          60
tctcttatat ataaaggcct gatcacgact tccaga atg ttt cca aaa ttc tca           114
                                      Met Phe Pro Lys Phe Ser
                                        1               5 ttt ctc ctg ata ttt gca gtt gtt ttg agt ctc act cat aag tcc tta           162
Phe Leu Leu Ile Phe Ala Val Val Leu Ser Leu Thr His Lys Ser Leu
            10                  15                  20 tgt caa gac tgg ctt acg ttt cag aag aag cac ctg aca aac acc cgg           210
Cys Gln Asp Trp Leu Thr Phe Gln Lys Lys His Leu Thr Asn Thr Arg
         25                  30                  35 gat gtt gac tgt aat aat atc atg tca aca aac ttg ttc cac tgc aag           258
Asp Val Asp Cys Asn Asn Ile Met Ser Thr Asn Leu Phe His Cys Lys
     40                  45                  50 gac aag aac act ttt atc tat tca cgt cct gag cca gtg aag gcc atc           306
Asp Lys Asn Thr Phe Ile Tyr Ser Arg Pro Glu Pro Val Lys Ala Ile
 55                  60                  65                  70 tgt aaa gga att ata gcc tcc aaa aat gtg tta act acc tct gag ttt           354
Cys Lys Gly Ile Ile Ala Ser Lys Asn Val Leu Thr Thr Ser Glu Phe
                 75                  80                  85 tat ctc tct gat tgc aat gta aca agc agg cct tgc aag tat aaa tta           402
Tyr Leu Ser Asp Cys Asn Val Thr Ser Arg Pro Cys Lys Tyr Lys Leu
             90                  95                 100 aag aaa tca act aat aca ttt tgt gta act tgt gag aat caa gct cca           450
Lys Lys Ser Thr Asn Thr Phe Cys Val Thr Cys Glu Asn Gln Ala Pro
        105                 110                 115 gta cat ttc gtg ggt gtc gga cat tgc tagaaatatg tttgacaaca                 497
Val His Phe Val Gly Val Gly His Cys
    120                 125 gggatgtgat aagcagctgc aagaaattat tttgaagtga atttactaaa gacactaatt         557
ttgcataaat tttccccaga gcttaccggt agtaagaaaa ttcaacagg gagccaagca          617 cagaaagtaa actaaggagc caaagtaatt ataaaagtca cactggaccg ctgctactgc         677
actcagatga ccaaatgaga aacagacaaa aacagcagag ttgggaagcg cagatccggg         737
aggtggcggg gagtcaattg gggatggagt ccatgtgaga tttggaaccg tttgttgctg         797
gtgaagcatg tggccggtgc acagtacaca tggggaaaga tagtcggatt ggccgggctc         857
gctgtggtgg tgccggcgt tgagccaaag gtggtgggga gatggctgtc ccccttctg          917 tggggctgt ggacagaggg agctgcggac caggggtggg aggcctggag agaattttca         977
aacagctgac gtgccgggg ctgggcagca tcggggaggg gaagggctgg gctcagatcc         1037
aggaagcatg gtcactgtat gaccagagtg gaagatggca gagccgctgc agtggccggg        1097
gagaccagag ggatcgtgc ccagcctttc ccctccctga tgtggccgt ttttggttat         1157 ggtaaccgct cccagctgtt tggggtgtt ttcgggcttc gcattttgg tctgcggctc          1217 cctctgtcca cggccctcat ggaggggggg tgggcatttc tccaccgcct ttggctctgt        1277
tgctggcact gtcgcagcga gtttggccag tcatggctca ttttcccatt tgtcatgtgt       1337
gttggttgca tgttttgtcg gcggtggact gttttgaatt tcacatggat tccatcttcg       1397
gttggttcct tgccacctcc tggatctgtg ctttccaatt ctgttttttc cccagcgctt       1457
```

-continued

```
agtggatgca gtgaaactct ggtgattacc atcatccaat catgtgcaag aaaaaatatt    1517
ttcatatttc ttccacccaa ttgggtattc attaggaagt ttgagcacat tcacgttcta    1577
gggaaaatga gtgcaactgc acttccaaag ttcacagtct atttgccttt agtaaatcca    1637
ccccattatt tctgagcaga ggacaaatct atggcaacaa aaaaacttta cctactgaat    1697
tattttatat tgattgaaga taatctttct ttcatttcct aaatattgta atcaaaatta    1757
atacataaca gctatgtatt ataccacagc agcaaatgtt aaaatagttt taaacgtaaa    1817
atatgtttta cctaaagtg gaagtaaact tctatcacta aattttacct ataggtgaga     1877
cccatgcgct cttcaggaat ggccgctggt gctgttcctt cagagccctg tgctgcgaac    1937
ggcggctccc gtgtgcatgt acaggagtga cgtcatcaca gctccggcca gtcacagagt    1997
tagagttcaa gtgtgagtgg cttgagccac gatgatgtcg ctcccaaaca tgtgtgcggg    2057
ggtctccgtt tgcggcgcag gacactgggg aatagcatg ggtgtgccgt tccttcagag     2117
catatgcgtg ggtgacgtca ctagctgcat ctaaagtaat atctcctaaa caatgcacat    2177
ttaggagata gttacagtac ctatgggtaa gccttattgt aggcttacct ataggtaaaa    2237
atcatgcatg ggagtttact tccatgtagg gatgaggaga gcaggctgac atattaaagt    2297
aaaaatctta cctatgtagg gatgaggaga gcaggctgac atattaaagt aaaaatctta    2357
cctatagtgg ttgaaagtag ttgaaaataa gatggcctgc agggtcttaa aaaggctagg    2417
atagcacagt atccacatga ggcaccagat ctcgctcccc cacacatgag tagcaaggag    2477
caatggtaat gtgagtttct taggctcgac cgttaaatag cgttggccct ccaagtgata    2537
catgggagat aagcagatgt ccgcgtatgc acgcagacat atgtgggcgg atgttgggat    2597
aggacgatca gagagatgct cagatctgcc cgaaggagaa aggtggaaac atccattcaa    2657
tgtcatatgc ctaaagaagc cacccaccat aaaaagttaa tagatcatca ggtggcagcc    2717
aaccacacca ggcccaaagg agggtggccc cagtgaaccg tataggaaca gcactcagct    2777
atcacataat tacacaagag tatagagacc cattgtgggt attaacaacc aaatggctaa    2837
aaaaaaaaaa aaaaaaaa                                                   2855
```

<210> SEQ ID NO 28
<211> LENGTH: 127
<212> TYPE: PRT
<213> ORGANISM: Rana pipiens
<220> FEATURE:
<223> OTHER INFORMATION: Rana pipiens ribonuclease (RaPLR1) Clone
      5a1b cDNA insert

<400> SEQUENCE: 28

```
Met Phe Pro Lys Phe Ser Phe Leu Leu Ile Phe Ala Val Val Leu Ser
  1               5                  10                  15

Leu Thr His Lys Ser Leu Cys Gln Asp Trp Leu Thr Phe Gln Lys Lys
             20                  25                  30

His Leu Thr Asn Thr Arg Asp Val Asp Cys Asn Asn Ile Met Ser Thr
         35                  40                  45

Asn Leu Phe His Cys Lys Asp Lys Asn Thr Phe Ile Tyr Ser Arg Pro
     50                  55                  60

Glu Pro Val Lys Ala Ile Cys Lys Gly Ile Ile Ala Ser Lys Asn Val
 65                  70                  75                  80

Leu Thr Thr Ser Glu Phe Tyr Leu Ser Asp Cys Asn Val Thr Ser Arg
                 85                  90                  95

Pro Cys Lys Tyr Lys Leu Lys Lys Ser Thr Asn Thr Phe Cys Val Thr
```

```
              100                 105                 110
Cys Glu Asn Gln Ala Pro Val His Phe Val Gly Val Gly His Cys
        115                 120                 125
```

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence:CAAX
      motif to target heterologous proteins to the plasma
      membrane, where A = aliphatic amino acid and
      X = Ser, Met, Cys, Ala or Gln

<400> SEQUENCE: 29

```
Cys Val Ile Met
  1
```

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence:Rana
      pipiens Onconase degenerate forward primer

<400> SEQUENCE: 30
agrgatgtkg attgygataa yatcatg                                    27

<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence:Rana
      pipiens Onconase degenerate reverse primer

<400> SEQUENCE: 31
aaartgmacw ggkgcctgrt tytcaca                                    27

<210> SEQ ID NO 32
<211> LENGTH: 96
<212> TYPE: DNA
<213> ORGANISM: Artificial Sequence
<220> FEATURE:
<223> OTHER INFORMATION: Description of Artificial Sequence:Rana
      catesbeiana ribonuclease synthetic gene (RaCOR1)
      oligonucleotide

<400> SEQUENCE: 32
cagaactggg ctactttcca gcagaaacat atcatcaaca ctccgatcat ctgcaacact    60
atcatggaca acaacatcta catcgttggt ggtcag                              96

<210> SEQ ID NO 33
<211> LENGTH: 86
<212> TYPE: DNA
<213> ORGANISM: Artificial Sequence
<220> FEATURE:
<223> OTHER INFORMATION: Description of Artificial Sequence:Rana
      catesbeiana ribonuclease synthetic gene (RaCOR1)
      oligonucleotide

<400> SEQUENCE: 33
tacatcgttg gtggtcagtg caaacgtgtt aacactttca tcatctctct gctactactg    60
ttaaacgtat ctgcactggt gttatc                                         86

<210> SEQ ID NO 34
<211> LENGTH: 96
<212> TYPE: DNA
<213> ORGANISM: Artificial Sequence
<220> FEATURE:
<223> OTHER INFORMATION: Description of Artificial Sequence:Rana
      catesbeiana ribonuclease synthetic gene (RaCOR1)
      oligonucleotide

<400> SEQUENCE: 34
atctgcactg gtgttactaa catgaacgtt ctgtctacta ctcgtttcca gctgaacact    60
tgcactcgta cttctatcac tccgcgtccg tgcccg                             96

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence:Rana
      catesbeiana ribonuclease synthetic gene (RaCOR1)
      oligonucleotide

<400> SEQUENCE: 35
gttgataaca ccagtgcaga t                                             21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence:Rana
      catesbeiana ribonuclease synthetic gene (RaCOR1)
      oligonucleotide

<400> SEQUENCE: 36
atctgcactg gtgttatcaa c                                             21

<210> SEQ ID NO 37
<211> LENGTH: 95
<212> TYPE: DNA
<213> ORGANISM: Artificial Sequence
<220> FEATURE:
<223> OTHER INFORMATION: Description of Artificial Sequence:Rana
      catesbeiana ribonuclease synthetic gene (RaCOR1)
      oligonucleotide

<400> SEQUENCE: 37
actccgcgtc cgtgcccgta ctcttctcgt actgaaacta actacatctg cgttaaatgc    60
gaaaaccagt acccggttca tttcgctggt atcgg                              95

<210> SEQ ID NO 38
<211> LENGTH: 71
<212> TYPE: DNA
<213> ORGANISM: Artificial Sequence
<220> FEATURE:
<223> OTHER INFORMATION: Description of Artificial Sequence:Rana
      catesbeiana ribonuclease synthetic gene (RaCOR1)
      oligonucleotide

<400> SEQUENCE: 38
atatatctag aaataatttt atttaacttt aagaaggaga tatacatatg cagaactggg    60
ctactttcca g                                                        71

<210> SEQ ID NO 39
<211> LENGTH: 48

```
<212> TYPE: DNA
<213> ORGANISM: Artificial Sequence
<220> FEATURE:
<223> OTHER INFORMATION: Description of Artificial Sequence:Rana
      catesbeiana ribonuclease synthetic gene (RaCOR1)
      oligonucleotide

<400> SEQUENCE: 39
cgcgccggat ccctactacg ggcaacgacc gataccagcg aaatgaac                    48

<210> SEQ ID NO 40
<211> LENGTH: 96
<212> TYPE: DNA
<213> ORGANISM: Artificial Sequence
<220> FEATURE:
<223> OTHER INFORMATION: Description of Artificial Sequence:Rana
      catesbeiana ribonuclease synthetic gene (RaCOR1)
      oligonucleotide

<400> SEQUENCE: 40
cagaactggg ctactttcca gcagaaacat atcatcaaca ctccgatcat ctgcaacact       60
atcctgcaga acaacatcta catcgttggt ggtcag                                 96

<210> SEQ ID NO 41
<211> LENGTH: 96
<212> TYPE: DNA
<213> ORGANISM: Artificial Sequence
<220> FEATURE:
<223> OTHER INFORMATION: Description of Artificial Sequence:Rana
      catesbeiana ribonuclease synthetic gene (RaCOR1)
      oligonucleotide

<400> SEQUENCE: 41
atctgcactg gtgttatcaa cctgaacgtt ctgtctacta ctcgtttcca gctgaacact       60
tgcactcgta cttctatcac tccgcgtccg tgcccg                                 96

<210> SEQ ID NO 42
<211> LENGTH: 33
<212> TYPE: DNA
<213> ORGANISM: Artificial Sequence
<220> FEATURE:
<223> OTHER INFORMATION: Description of Artificial Sequence:Rana
      catesbeiana insertion primer for NdeI restriction
      site

<400> SEQUENCE: 42
ggattccata tgcagaactg ggctattttc cag                                    33

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence:six
      histidine residue tag at amino terminus

<400> SEQUENCE: 43

His His His His His His
 1               5
```

RECOMBINANT ANTI-TUMOR RNASE

CROSS REFERENCE TO RELATED APPLICATIONS

This application is a continuation of U.S. application Ser. No. 09/622,613, filed Jul. 31, 2001, which is incorporated by reference, and now issued as U.S. Pat. No. 6,869,604; which is a national stage of PCT/US99/06641, filed Mar. 26, 1999; which claims benefit of U.S. application Ser. No. 60/079,751, filed Mar. 27, 1998.

FEDERALLY SPONSORED RESEARCH AND DEVELOPMENT

Not applicable.

BACKGROUND OF THE INVENTION

Ribonucleases such as ribonuclease A ("RNase A") and their cytotoxicity towards tumor cells were discovered in the 1960s (reviewed in Roth, J., *Cancer Res.* 23:657–666 (1963)). In the 1970s, human serum was also discovered to contain several RNAses that are expressed in a tissue specific manner (Reddi, E., *Biochem. Biophys. Res. Commun.* 67:110–118 (1975); and Blank, et al., HUMAN BODY FLUID RIBONUCLEASES: DETECTION, INTERRELATIONSHIPS AND SIGNIFICANCE, pp 203–209 (IRL Press, London, 1981)).

Further to these early studies was the discovery that an anti-tumor protein from oocytes of *Rana pipiens* had homology to RNAse A (Ardelt, et al., *J. Biol. Chem.* 256:245–251 (1991)). This protein was termed ONCONASE®, Alfacell Corporation, N.J. See also e.g., Darzynkiewicz, et al., *Cell Tissue Kinet.* 21:169–182 (1988); Mikulski, et al., *Cell Tissue Kinet.* 23:237–246 (1990); and U.S. Pat. No. 4,888,172).

Phase I and Phase I/II clinical trials of ONCONASE® as a single therapeutic agent in patients with a variety of solid tumors (Mikulski, et al., *Int. J. of Oncology* 3: 57–64 (1993)) or combined with tamoxifen in patients with advanced pancreatic carcinoma have been completed (Chun, et al., *Proc. Amer. Soc. Clin. Oncol.* 14:210 (1995)) and the protein has been found to be efficacious in pancreatic, renal cell, and prostate cancers as well as mesothelioma.

Conjugation of ONCONASE® to cell-type-specific ligands was found to increase its potency towards tumor cells (Rybak, et al., *Drug Delivery* 1:3–10 (1993)). Taken together, these results indicated that ONCONASE® has properties advantageous to the generation of a potent selective cell killing agent.

Development of ONCONASE® conjugates for human therapeutics has been slow. ONCONASE® is derived from amphibian tissue and trace contaminants present in the purified preparation stimulate undesirable immune responses in humans. This side-effect has led to production of a recombinant form of the protein (Newton, et al., *Protein Engineering* 10:463–470 (1997) and PCT published application WO 97/38112).

However, expression of active recombinant ONCONASE® has been problematic. ONCONASE® requires a pyroglutamic acid at the N-terminus for activity. Unfortunately, ONCONASE® with a N-terminal glutamine is not expressed by bacteria but accumulates in insoluble inclusion bodies. To increase bacterial expression of soluble ONCONASE®, methionine has been appended to the N-terminus. However, this modification of the protein prevents the formation of the pyroglutamic acid necessary for activity. Therefore, it has been necessary to engineer ONCONASE® with an N-terminal methionine only to remove it for activity. The cleaved and the uncleaved proteins must then be separated to obtain a pure composition of high purity and activity.

Other problems have arisen in the manufacture of ONCONASE®-based fusion proteins. It has been difficult to fuse recombinant ONCONASE® in frame to ligand binding moieties and retain proper folding of both the ONCONASE® and the ligand binding moiety. This has limited the use of ONCONASE® in targeted cell killing to only those compounds that can be chemically conjugated.

Thus, there exists in the art a need for recombinant ribonucleases that can be expressed in bacteria and retain activity. Furthermore, there exists a need for a ribonuclease with anti-tumor activity that retains its activity when produced as a single chain fusion protein. This invention fulfills these and other needs.

SUMMARY OF THE INVENTION

This invention provides for new recombinant ribonuclease proteins. The proteins, unlike ONCONASE®, are expressed well by bacteria without an N-terminal methionine. This is due largely to the presence of a signal peptide that is cleaved by the bacteria. The ribonucleases are then secreted into the bacterial media. The soluble expression of these ribonucleases allows the proteins of this invention to be fused in-frame with ligand binding moieties to form cytotoxic fusion proteins.

Specifically, this invention provides for a ribonuclease expressed from recombinant DNA that has (a) measurable ribonuclease activity; (b) an amino terminal end beginning with a glutamine or a glutamine cyclized to a pyroglutamic acid; (c) a leucine at position 11; an asparagine at position 21, a threonine at position 85, and a histidine at position 103, such positions being determined with reference to those specified amino acid positions of SEQ ID NO:2; and (d) is substantially identical to SEQ ID NO:2. In one embodiment, the ribonuclease is expressed with a methionine at the 1 position (SEQ ID NO:6). In another, more preferred embodiment, the ribonuclease is expressed with a methionine at the 1 position and an amino acid change from methionine to leucine at position 24 (SEQ ID NO:8). In the most preferred embodiment, the ribonuclease is expressed with histidine residues at positions 1 to 6, a methionine at 7 and a leucine at position 30 (SEQ ID NO:9). In alternative embodiment of the invention, the glutamine at position 1 is replaced with a serine (SEQ ID NO:11).

In another embodiment relating to SEQ ID NO:2, the ribonuclease is transcribed and translated with a signal peptide (SEQ ID NO:28). Post-translation modification by the expressing cell cleaves the signal peptide from the ribonuclease and the protein is secreted by the host cell.

In another embodiment of the invention, ribonucleases encoded by the nucleic acid sequence of SEQ ID NO:14 and conservative variants thereof are claimed. Within this embodiment are the amino acid sequences of SEQ ID NO:17, SEQ ID NO:19, SEQ ID NO:21, SEQ ID NO:24 and SEQ ID NO:26. This ribonuclease can also be engineered to comprise the signal sequence mentioned above.

Also encompassed within this invention are cytotoxic reagents comprising the ribonucleases with or without the conservative substitutions listed above linked to a ligand binding moiety. In one embodiment, the linkage is through a covalent bond. In a preferred embodiment, the covalent bond is at the carboxy terminus of the ribonuclease.

In one aspect of this embodiment, the ribonucleases of this invention are linked to hCG. This has been found to be efficaceous against Kaposi's Sarcoma cells.

In another aspect of this embodiment, the ligand binding moiety is an antibody directed against a cell surface antigen present on a cancer cell. In a preferred aspect, the antibody is a recombinant single chain antibody directed against a cell surface antigen on a cancerous B cell, in particular, CD22. In a most preferred aspect, the ligand binding moiety is LL2.

In yet another embodiment, a method is provided which prepares a substantially pure ribonuclease of this invention. In addition, the method can be used to purify a cytotoxic reagent of this invention. The method comprises: (i) contacting a ribonuclease with an ($His_6$) (SEQ ID NO: 43) histidine tag and a methionine at position 7 with an effective concentration of a cleaving agent such that the ribonuclease is cleaved after the carboxy group of methionine at position 1; (ii) passing the ribonuclease through a Ni2+-NTA agarose column; and (iii) eluting the substantially pure ribonuclease from the column. In a preferred embodiment, the cleaving agent is CNBr.

In still another embodiment of this invention, pharmaceutical compositions are provided which comprise a ribonuclease expressed from recombinant DNA. The ribonucleases are selected from the group consisting of SEQ ID NO:2, SEQ ID NO:4, SEQ ID NO:6, SEQ ID NO:8, SEQ ID NO:11, SEQ ID NO:13, SEQ ID NO:15, SEQ ID NO:17, SEQ ID NO:19, SEQ ID NO:21, SEQ ID NO:24 and SEQ ID NO:26 in a pharmaceutically acceptable carrier. In one aspect of this embodiment, the pharmaceutical composition also contains an antineoplast, preferably Adriamycin.

In another embodiment, pharmaceutical compositions are provided which comprise the ribonucleases of this invention linked to a ligand binding moiety. As above, the pharmaceutical composition may contain an antineoplast, preferably Adriamycin.

In yet another embodiment of this invention, a method is provided for killing cancer cells. The method comprises contacting cells to be killed with a ribonuclease expressed by recombinant DNA and having a sequence selected from the group consisting of SEQ ID NO:2, SEQ ID NO:4, SEQ ID NO:6, SEQ ID NO:8, SEQ ID NO:11, SEQ ID NO:13, SEQ ID NO:15, SEQ ID NO:17, SEQ ID NO:19, SEQ ID NO:21, SEQ ID NO:24 and SEQ ID NO:26. In addition, the method also comprises contacting cells to be killed with a cytotoxic reagent comprising the ribonucleases listed above linked to a ligand binding moiety. In a preferred embodiment, the cancer cell to be killed is a malignant B cell and the ligand binding moiety is an antibody. In a preferred aspect, the antibody is a single chain antibody directed against CD22. In a most preferred embodiment, the antibody is LL2.

DETAILED DESCRIPTION OF THE INVENTION

I. Definitions

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, N.Y. (1991) provide one of skill with a general dictionary of many of the terms used in this invention. Although any methods and materials similar or equivalent to those described herein can be used in the practice or testing of the present invention, the preferred methods and materials are described. Numeric ranges are inclusive of the numbers defining the range. Unless otherwise indicated, nucleic acids are written left to right in 5' to 3' orientation; amino acid sequences are written left to right in amino to carboxy orientation, respectively. The headings provided herein are not limitations of the various aspects or embodiments of the invention which can be had by reference to the specification as a whole. Accordingly, the terms defined immediately below are more fully defined by reference to the specification as a whole.

The terms "isolated," "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated ribonuclease nucleic acid is separated from open reading frames that flank the ribonuclease gene and encode proteins other than ribonuclease. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

"Nucleic acid" refers to deoxyribonucleotides or ribonucleotides and polymers thereof in either single- or double-stranded form. Unless specifically limited, the term encompasses nucleic acids containing known analogs of natural nucleotides, which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer, et al., *Nucleic Acid Res.* 19:5081 (1991); Ohtsuka, et al., *J. Biol. Chem.* 260:2605–2608 (1985); and Rossolini, et al., *Mol. Cell. Probes* 8:91–98 (1994)). The term nucleic acid is used interchangeably with gene, cDNA, and mRNA encoded by a gene.

The terms "polypeptide," "peptide" and "protein" are used interchangeably herein to refer to a polymer of amino acid residues. The terms apply to amino acid polymers in which one or more amino acid residue is an artificial chemical analog of a corresponding naturally occurring amino acid, as well as to naturally occurring amino acid polymers.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

(see, e.g., Creighton, Proteins (1984)).

"Pyroglutamic acid" is the cyclized internal amide of L-glutamic acid with the following structure:

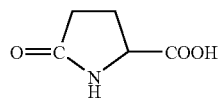

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

A "labeled nucleic acid probe or oligonucleotide" is one that is bound, either covalently, through a linker, or through ionic, van der Waals or hydrogen bonds to a label such that the presence of the probe may be detected by detecting the presence of the label bound to the probe.

"Amplification" primers are oligonucleotides comprising either natural or analog nucleotides that can serve as the basis for the amplification of a select nucleic acid sequence. They include, e.g., polymerase chain reaction primers and ligase chain reaction oligonucleotides.

The term "recombinant" when used with reference, e.g., to a cell, or nucleic acid, or vector, indicates that the cell, or nucleic acid, or vector, has been modified by the introduction of a heterologous nucleic acid or the alteration of a native nucleic acid, or that the cell is derived from a cell so modified. Thus, for example, recombinant cells express genes that are not found within the native (non-recombinant) form of the cell or express native genes that are otherwise abnormally expressed, under expressed or not expressed at all.

The term "identical" in the context of two nucleic acids or polypeptide sequences refers to the residues in the two sequences that are the same when aligned for maximum correspondence, as measured using one of the following "sequence comparison algorithms."

One example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35:351–360 (1987). The method used is similar to the method described by Higgins & Sharp, *CABIOS* 5:151–153 (1989). The program can align up to 300 sequences of a maximum length of 5,000. The multiple alignment procedure begins with the pairwise alignment of the two most similar sequences, producing a cluster of two aligned sequences. This cluster can then be aligned to the next most related sequence or cluster of aligned sequences. Two clusters of sequences can be aligned by a simple extension of the pairwise alignment of two individual sequences. The final alignment is achieved by a series of progressive, pairwise alignments. The program can also be used to plot a dendrogram or tree representation of clustering relationships. The program is run by designating specific sequences and their amino acid or nucleotide coordinates for regions of sequence comparison. Another example of an algorithm that is suitable for determining sequence similarity is the BLAST algorithm, which is described in Altschul, et al., *J. Mol. Biol.* 215:403–410 (1990). Software for performing BLAST analyses is publicly available through the National Center for Biotechnology Information. This algorithm involves first identifying high scoring sequence pairs (HSPs) by identifying short words of length W in the query sequence that either match or satisfy some positive-valued threshold score T when aligned with a word of the same length in a database sequence. T is referred to as the neighborhood word score threshold (Altschul, et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm performs a statistical analysis of the similarity between two sequences (see, e.g., Karlin & Altschul, *Proc. Nat'l Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to an ribonuclease nucleic acid if the smallest sum probability in a comparison of the test nucleic acid to an ribonuclease nucleic acid is less than about 0.1, more preferably less than about 0.01, and most preferably less than about 0.001. Where the test nucleic acid encodes a ribonuclease polypeptide, it is considered similar to a specified ribonuclease nucleic acid if the comparison results in a smallest sum probability of less than about 0.5, and more preferably less than about 0.2.

The phrase "substantially identical" in the context of two nucleic acids or polypeptides thus typically means that a polynucleotide or polypeptide comprises a sequence that has at least 60% sequence identity, preferably at least 80%, more preferably at least 90% and most preferably at least 95%, compared to a reference sequence using the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection. One indication that two nucleic acid sequences or polypeptide are substantially identical is that the polypeptide which the first nucleic acid encodes is immunologically cross reactive with the polypeptide encoded by the second nucleic acid. Thus, a polypeptide is substantially identical to a second polypeptide, for example, where the two peptides differ only by a conservative substitution. Another indication that two nucleic acid sequences are substantially identical is that the two molecules hybridize to each other under stringent conditions.

The phrase "determined with reference to" in the context of identifying changes in amino acid sequence means that the amino acid as indicated in the sequence listing at that position is changed to the amino acid indicated. For example, in some embodiments of this invention the methionine corresponding to position 23 of SEQ ID NO:2 is changed to a leucine. In SEQ ID NO:2, a methionine is at position 23. In SEQ ID NO:8, the methionine at position 23 in SEQ ID NO:2 corresponds to a methionine at position 24 which has been changed to a leucine.

The phrase "selectively hybridizes to" refers to the binding, duplexing, or hybridizing of a molecule only to a particular nucleotide sequence under stringent hybridization conditions when that sequence is present in a complex mixture (e.g., total cellular) DNA or RNA. The phrase "stringent hybridization conditions" refers to conditions under which a probe will hybridize to its target subsequence, but to no other sequences. Stringent conditions are sequence-dependent and will be different in different circumstances. Longer sequences hybridize specifically at higher temperatures. An extensive guide to the hybridization of nucleic acids is found in Tijssen, TECHNIQUES IN BIOCHEMISTRY AND MOLECULAR BIOLOGY—HYBRIBIZATION WITH NUCLEIC PROBES, "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents as formamide.

"Antibody" refers to a polypeptide substantially encoded by an immunoglobulin gene or immunoglobulin genes, or fragments thereof which specifically bind and recognize an antigen. The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50–70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially an Fab with part of the hinge region (see, FUNDAMENTAL IMMUNOLOGY, 3D ED., Paul (ed.) 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies or those synthesized de novo using recombinant DNA methodologies (e.g., single chain Fv).

The phrase "single chain Fv" or "scFv" refers to an antibody in which the heavy chain and the light chain of a traditional two chain antibody have been joined to form one chain. Typically, a linker peptide is inserted between the two chains to allow for proper folding and creation of an active binding site.

The term "linker peptide" includes reference to a peptide within an antibody binding fragment (e.g., Fv fragment) which serves to indirectly bond the variable heavy chain to the variable light chain.

The term "contacting" includes reference to placement in direct physical association. With regards to this invention, the term refers to antibody-antigen binding.

An "anti-ribonuclease" antibody is an antibody or antibody fragment that specifically binds a polypeptide encoded by the ribonuclease gene, cDNA, or a subsequence thereof.

An "immunoconjugate" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

A "fusion protein" or when a molecule is "linked" to another refers to a chimeric molecule formed by the joining of two or more polypeptides through a bond formed one polypeptide and another polypeptide. The bond may be covalent or noncovalent. An example of a covalent bond is the chemical coupling of the two polypeptides to form peptide bond. Examples of non-covalent bond are hydrogen bonds, electrostatic interactions and van der Waal's forces.

If the bond is by a peptide bond, the fusion protein may be expressed as a single polypeptide from a nucleic acid sequence encoding a single contiguous fusion protein. A single chain fusion protein is a fusion protein having a single contiguous polypeptide backbone.

A "ligand" or a "ligand binding moiety", as used herein, refers generally to all molecules capable of specifically delivering a molecule, reacting with or otherwise recognizing or binding to a receptor on a target cell. Specifically, examples of ligands include, but are not limited to, immunoglobulins or binding fragments thereof, lymphokines, cytokines, cell surface antigens such as CD22, CD4 and CD8, solubilized receptor proteins such as soluble CD4, hormones, growth factors such as epidermal growth factor (EGF), and the like which specifically bind desired target cells.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, antibodies raised to ribonuclease with the amino acid sequence encoded in SEQ ID NO:2 can be selected to obtain only those antibodies that are specifically immunoreactive with ribonuclease and not with other proteins, except for polymorphic variants, alleles, and closely related interspecies homologs of ribonuclease. This selection may be achieved by subtracting out antibodies that cross react with molecules such as ONCONASE®. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, ANTIBODIES, A LABORATORY MANUAL (1988), for a description of immunoassay formats and conditions that can be used to determine specific immunoreactivity). Typically a specific or selective reaction will be at least twice background signal or noise and more typically more than 10 to 100 times background.

"Cytotoxicity", as used herein, refers to the inhibition of protein synthesis in human tumor cells, e.g., HS578T (ATCC No. HTB 126) using the protocol described in Rybak, et al., *JNCI* 88:747–753 (1996). A "cytotoxic reagent" of the present invention will have a relative 50% inhibitory concentration ($IC_{50}$) at least 50% that of an equimolar amount of the polypeptide of SEQ ID NO:2. More preferably, the relative $IC_{50}$ will be at least 60% or 70% that of the polypeptide of SEQ ID NO:2, and even more preferably, at least 100%.

II. Introduction

This invention provides highly active and cytotoxic ribonuclease molecules which can be used to selectively kill and target cells, particularly tumor cells. In some embodiments the molecules are designed to fold into more cytotoxic molecules and in other embodiments, the molecules are designed for better expression in bacteria.

The ribonucleases of this invention are isolated from members of the genus *Rana*. SEQ ID NO:1 represents the nucleic acid sequence of a RNAse derived from a *Rana pipiens* liver mRNA library. The corresponding amino acid sequence is represented by SEQ ID NO:2 (RaPLR1). SEQ ID NO:6 is the amino acid sequence of RaPLR1 but with a methionine at the 1 position. SEQ ID NO:4 is the amino acid sequence of RaPLR1 but with a leucine at position 23 (instead of a methionine). SEQ ID NO:8 represents the sequence shown in SEQ ID NO:4 but with a methionine at the 1 position. SEQ ID NO:9 represents a protein with the amino acid sequence of SEQ ID NO:8 but with a six histidine residue tag at the amino terminus. SEQ ID NO:11 represents RAPLR1 with a serine at the N-terminus and SEQ ID NO:13 represents RaPLR1 with a serine at the 2 position and a methionine at the 1 position. SEQ ID NO:28 is the amino acid sequence of RAPLR1 with the signal peptide at the N-terminus.

In addition to ribonuclease derived from *Rana pipiens*, this invention also encompasses ribonucleases derived from *Rana catesbeiana* oocytes. Although the amino acid sequence of *Rana catesbeiana* oocyte RNAse (RaCOR1) has been known since 1989 (Nitta, R., et al., *J. Biochem.* 106:729 (1989); Okabe, Y., et al., *J. Biochem* 109:786 (1991); Liao, Y, *Nucl., Acids Res.* 20:1371 (1992); Nitta, K., et al., *Glycobiology* 3:37 (1993); Liao, Y. & Wang, J., *Eur. J. Biochem.* 222:215 (1994); Wang, J., et al., *Cell Tissue Res.* 280:259 (1995); Liao, Y., et al., *Protein Expr. Purif.* 7:194 (1996); and Inokuchi, N., et al., *Biol. Pharm. Bull.* 20:471 (1997)), genomic DNA or mRNA which encodes the oocyte RNAse has not been discovered. An object of this invention was to deduce the nucleic acid sequence encoding this RNAse and express the RNAse recombinantly.

SEQ ID NO:14 represents the nucleic acid sequence of RaCOR1 but modified to use the preferred codons for *E. coli*, the expression system exemplified in this invention. SEQ ID NO:15 is the corresponding amino acid sequence. SEQ ID NO:17 is the same amino acid sequence as SEQ ID NO:15 but with a methionine at the 1 position. SEQ ID NO:19 is the amino acid sequence of SEQ ID NO:15 but with leucines substituted for methionines at positions 22 and 57. SEQ ID NO:21 is the same as SEQ ID NO:19 except for a methionine at the 1 position. SEQ ID NO:22 is the same as SEQ ID NO:21 except six histidine residues have been appended to the N-terminus. Finally, SEQ ID NO:24 represents RaCOR1 but with a serine at the N-terminus and SEQ ID NO:26 is the same as SEQ ID NO:24 except a methionine is at the 1 position.

Preferably, the ribonuclease molecules will have an amino terminal end selected from the group consisting of:
Gln-
Met-Gln;
Met-Ser;
Met-Thr;
Tyr; and
Pyroglutamic acid-.

Further, it is preferred that the ribonuclease molecules be modified so that the methionine of amino acid position 23 of SEQ ID NO:2 is deleted or replaced by Leu. In one embodiment of the invention, the methionines at position 22 and 57 of SEQ ID NO:15 are also replaced by a leucine.

In other alternative embodiments, the ribonuclease molecules will be fused at either the carboxyl or amino end to a ligand binding moiety, such as a single chain Fv which recognizes a cell surface antigen on a tumor cell. Other ligand binding moieties include, but are not limited to, other antibody fragments, receptors, antigens, lectins, cytokines, lipopolysaccharides and any other compound that binds to a cell.

Comparisons of the ribonuclease sequences provided here can be made to described sequences in the pancreatic RNAse A superfamily. Many of such members are known and include, but are not limited to, ONCONASE® (Ardelt, W. et al., *J. Biol. Chem.* 266:245 (1991)); eosinophil derived neurotoxin (EDN) and human eosinophil cationic protein (ECP) (Rosenberg, et al., *J. Exp. Med.* 170:163 (1989)); angiogenin (Ang) (Fett, J. W. et al., *Biochemistry* 24:5480 (1985)); bovine seminal RNase (Preuss, et al., *Nuc. Acids. Res.* 18:1057 (1990)); and bovine pancreatic RNase (Beintama, et al., *Prog. Biophys. Mol. Biol.* 51:165 (1988)). Amino acid sequence alignment for such RNAses are set out in Youle, et al., *Crit. Rev. Ther. Drug. Carrier Systems* 10:1–28 (1993).

III. Numbering of Amino Acid Residues

The amino acid sequence positions described herein, unless otherwise indicated, use as a frame of reference the RNAse sequences of the respective SEQ ID NOS: in the SEQUENCE LISTING. Residue numbers indicate the distance from the amino terminus. The amino acid sequence for SEQ ID NO:2 and for SEQ ID NO:15 are set forth in the SEQUENCE LISTING.

IV. RNAse Proteins

The present invention includes RNAse proteins comprising a polypeptide of SEQ ID NO:2 and 15 and conservative variants thereof. The polypeptides of the present invention (SEQ ID NO:2 and 15 and conservative variants thereof) demonstrate cytotoxic activity, as defined herein. The RNAse proteins of the present invention may be limited to the polypeptides of SEQ ID NO:2 and 15 and conservative variants thereof, or may be inclusive of additional amino acid residues linked via peptide bonds to the carboxy and/or amino termini of the polypeptide. Preferably, the conservative variants of SEQ ID NO:2 and 15 comprise a glutamine residue capable of spontaneous cyclization to pyroglutamic acid at the 1 position.

The RNAse proteins of this invention optionally are translated by the host cell with a signal peptide attached. The signal peptide is shown in SEQ ID NO:28. The presence of this sequence allows the host cell, in particular *E. coli*, to secrete soluble protein. In this configuration, the presence of a N-terminal methionine is not necessary for bacterial expression and the N-terminal residue is a glutamine or pyroglutamic acid. One of skill will recognize that other signal peptides may be appended to the RNAse proteins of this invention. The choice of signal peptide will depend on the expressing cell, the protein being expressed and the preference of the practitioner.

The polypeptide of SEQ ID NO:2 or conservatively modified variants thereof may have a leucine or other hydrophobic residue substituting for the methionine at position 23. The polypeptide of SEQ ID NO:15 or conservatively modified variants thereof may have a leucine or other hydrophobic residue substituting for the methionine at positions 22 and 57. Those of skill will recognize that a polypeptide lacking a methionine is typically not subject to specific cleavage using cyanogen bromide.

Proteins of the present invention can be produced by recombinant expression of a nucleic acid encoding the polypeptide followed by purification using standard techniques. Typically, the RNAse proteins are encoded and expressed as a contiguous chain from a single nucleic acid. The length of the RNAse proteins of the present invention is generally less than about 600 amino acids in length.

Recombinant RNAse proteins can also be synthetically prepared in a wide variety of well-known ways. Polypeptides of relatively short size are typically synthesized in solution or on a solid support in accordance with conventional techniques. See, e.g., Merrifield, *J. Am. Chem. Soc.* 85:2149–2154 (1963). Recombinantly produced or synthetic polypeptides can be condensed to form peptide bonds with other polypeptides or proteins formed synthetically or by recombinant methods. Various automatic synthesizers and sequencers are commercially available and can be used in accordance with known protocols. See, e.g., Stewart & Young, SOLID PHASE PEPTIDE SYNTHESIS, 2d. ed., Pierce Chemical Co. (1984).

A. RNAse Proteins Comprising Amino Terminal Methionine

The present invention also includes RNAse proteins comprising: 1) a polypeptide of SEQ ID NO:2 or SEQ ID NO:15 and conservatively modified variants thereof, and 2) a methionine at position 1 (see, e.g. SEQ ID NO:6 and SEQ ID NO:17). Isolated nucleic acids coding for the RNAse proteins of the present invention are also provided. Preferably, as in SEQ ID NO:2 and 15, the position 1 residues of the polypeptides are glutamines. Various embodiments of the polypeptide of SEQ ID NO:2 and 15 and conservative variants thereof may be employed in this aspect of the invention.

Those of skill will understand that an N-terminal methionine or formylmethionine (collectively, "methionine") is typically required for protein synthesis in a bacterial host cell. The N-terminal methionine may be directly linked to the amino acid of position 1 of the polypeptides of the present invention where position 1 is not methionine via a peptide bond. Alternatively, the methionine is indirectly or directly linked to the amino acid of position 1 of the polypeptides of the present invention via a plurality of peptide bonds from a contiguous chain of amino acid residues. The residues, extending and inclusive of the amino terminal methionine to the amino acid directly linked via a peptide bond to the amino terminal amino acid residue of the polypeptide, constitute an amino terminal peptide. Thus, the amino terminal peptide consists of all amino acid residues linked to position 1 of SEQ ID NO:2 or 15 or conservatively modified variants thereof. The N-terminal peptide is at least one amino acid residue in length (i.e., a methionine residue) or may be 5, 10, 20, 50, 100, 200, 300, 400, or more amino acids in length.

The N-terminal peptide may comprise a signal sequence for transport into various organelles or compartments of the host cell, or for transport into the surrounding media. The N-terminal peptide may also encode sequences which aid in purification such as epitopes which allow purification via immunoaffinity chromatography, e.g., a plurality of histidine residues) or sequences recognized by endoproteases such as Factor Xa. The N-terminal peptide may also recognize extracellular and intracellular targets, such as telomerase.

B. Making the RNAse Protein

The present invention is also directed to methods of making the RNAse polypeptides of SEQ ID NO:2, SEQ ID NO:15 and conservative variants thereof. The polypeptides of the SEQ ID NO:2 and 15 and conservative variants thereof may conveniently be assayed for cytotoxicity or anti-viral (e.g. HIV-1) inhibition by methods disclosed herein.

1. Expressing the RNAse Protein

This invention relies on routine techniques in the field of recombinant genetics. Basic texts disclosing the general methods of use in this invention include Sambrook, et al., MOLECULAR CLONING, A LABORATORY MANUAL, 2ND ED. (1989); Kriegler, GENE TRANSFER AND EXPRESSION: A LABORATORY MANUAL (1990); and Ausubel et al., (eds.), CURRENT PROTOCOLS IN MOLECULAR BIOLOGY (1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kD) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859–1862 (1981), using an automated synthesizer, as described in Van Devanter, et al., *Nucl. Acids Res.* 12:6159–6168 (1984). Purification of oligonucleotides is by either native acrylamide gel electrophoresis or by anion-exchange HPLC as described in Pearson & Regnier, *J. Chrom.* 255:137–149 (1983).

The sequence of the cloned genes and synthetic oligonucleotides can be verified after cloning using, e.g., the chain termination method for sequencing double-stranded templates of Wallace, et al., *Gene* 16:21–26 (1981).

In one embodiment of the invention, a RNAse of SEQ ID NO:4, 8, 9, 13, 17, 21, 22, 26 and conservative variants thereof wherein the nucleic acids encode an amino terminal methionine, are expressed in a host cell. Various aspects of the polypeptides of the present invention which have been previously described may be utilized in this aspect of the invention. By "host cell" is meant a cellular recipient, or extract thereof, of an isolated nucleic acid which allows for translation of the nucleic acid and requires an amino terminal methionine for translation of the nucleic acid into its encoded polypeptide. Eukaryotic and prokaryotic host cells may be used such as animal cells, insect cells, bacteria, fungi, and yeasts. Methods for the use of host cells in expressing isolated nucleic acids are well known to those of skill and may be found, for example, in Berger & Kimmel, GUIDE TO MOLECULAR CLONING TECHNIQUES, METHODS IN ENZYMOLOGY VOL. 152, Academic Press, Inc., San Diego, Calif. (Berger); Sambrook, et al., MOLECULAR CLONING—A LABORATORY MANUAL (2ND ED.) Vol. 1–3 (1989) and CURRENT PROTOCOLS IN MOLECULAR BIOLOGY, F. M. Ausubel et al., eds., Current Protocols, a joint venture between Greene Publishing Associates, Inc. and John Wiley & Sons, Inc., (1997 Supplement) (Ausubel). A variety of host cells and expression vectors are available from commercial vendors, or the American Type Culture Collection (Rockville, Md.). Accordingly, this invention also provides for host cells and expression vectors comprising the nucleic acid sequences described herein.

Nucleic acids encoding RNAse proteins can be made using standard recombinant or synthetic techniques. Nucleic acids may be RNA, DNA, or hybrids thereof. Given the polypeptides of the present invention, one of skill can construct a variety of clones containing functionally equivalent nucleic acids, such as nucleic acids which encode the same polypeptide. Cloning methodologies to accomplish these ends, and sequencing methods to verify the sequence of nucleic acids are well known in the art. Examples of appropriate cloning and sequencing techniques, and instructions sufficient to direct persons of skill through many cloning exercises are found in Berger & Kimmel; Sambrook et al.; and F. M. Ausubel et al. (all supra). Product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to one of skill.

The nucleic acid compositions of this invention, whether RNA, cDNA, genomic DNA, or a hybrid of the various combinations, are isolated from biological sources or synthesized in vitro. Deoxynucleotides may be synthesized chemically according to the solid phase phosphoramidite triester method described by Beaucage & Caruthers, *Tetrahedron Letts.* 22(20):1859–1862 (1981), e.g., using an automated synthesizer, e.g., as described in Needham-VanDevanter, et al., *Nucleic Acids Res.* 12:6159–6168 (1984).

In one embodiment of the invention, the amino acid sequence of RaCOR1, which had been previously published, was used to deduce a nucleic acid sequence and, using the preferred codon for the expressing cell, synthesized. For example, the RaCOR1 nucleic acid sequence was prepared from the published amino acid sequence of the native RNAse and the preferred codon usage by *E. coli*.

To generate the full length nucleic acid sequence, overlapping oligonucleotides, representing both the sense and nonsense strands of the gene and usually 40–120 bp in length, were synthesized chemically. These DNA fragments were then annealed, ligated and cloned. For example, from the published amino acid sequence of ribonuclease from *Rana catesbeiana* oocytes, a series of oligonucleotide primers were prepared. These primers (SEQ ID NO:32–41) were used to generate the 5' and 3' ends of ribonuclease. The two regions of nucleic acid were then ligated to form the complete coding sequence. An advantage of this method is that mutations are relatively easy to engineer. To do so, one changes the nucleotides within the synthetic primer to correspond to the codon that translates to the desired amino acid.

One of skill will recognize many other ways of generating alterations or variants of a given nucleic acid sequence. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, Giliman & Smith, *Gene* 8:81–97 (1979), Roberts, et al., *Nature* 328:731–734 (1987) and Sambrook, Innis, Ausubel, and Berger (all supra).

In another embodiment of the present invention, site directed mutagenesis is used to change an interior methionine to a leucine. The nucleic acid sequence is changed by synthesizing an oligonucleotide primer that contains the mutation. The primer is hybridized to a nucleic acids of SEQ ID NO:1 and SEQ ID NO:14 and a new sequence amplified. After suitable rounds of amplification (approximately 20–30), the overwhelming majority of the sequences contain the mutation. The amplification product with the mutation is ligated into an expression vector and the RNAse with the mutation expressed.

Most commonly, polypeptide sequences are altered by changing the corresponding nucleic acid sequence and expressing the polypeptide. However, polypeptide sequences can also be generated synthetically using commercially available peptide synthesizers to produce any desired polypeptide (see, Merrifield, and Stewart & Young, supra).

One of skill can select a desired nucleic acid or polypeptide of the invention based upon the sequences provided and upon knowledge in the art regarding ribonucleases generally. The physical characteristics and general properties of RNAses are known to skilled practitioners. The specific effects of some mutations in RNAses are known. Moreover, general knowledge regarding the nature of proteins and nucleic acids allows one of skill to select appropriate sequences with activity similar or equivalent to the nucleic acids and polypeptides disclosed in the sequence listings herein. The definitions section herein describes exemplary conservative amino acid substitutions.

Finally, most modifications to nucleic acids and polypeptides are evaluated by routine screening techniques in suitable assays for the desired characteristic. For instance, changes in the immunological character of a polypeptide can be detected by an appropriate immunological assay. Modifications of other properties such as nucleic acid hybridization to a target nucleic acid, redox or thermal stability of a protein, thermal hysteresis, hydrophobicity, susceptibility to proteolysis, or the tendency to aggregate are all assayed according to standard techniques.

To obtain high level expression of a cloned gene, such as those cDNAs encoding ribonuclease, it is important to construct an expression vector that contains a strong promoter to direct transcription, a transcription/translation terminator, and a ribosome binding site for translational initiation. Suitable bacterial promoters are well known in the art and described, e.g., in Sambrook et al. and Ausubel et al. Bacterial expression systems for expressing ribonuclease are available in, e.g., *E. coli*, *Bacillus* sp., and *Salmonella* (Palva, et al., *Gene* 22:229–235 (1983); Mosbach, et al., *Nature* 302:543–545 (1983). Kits for such expression systems are commercially available. Eukaryotic expression systems for mammalian cells, yeast, and insect cells are well known in the art and are also commercially available.

The promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the ribonuclease-encoding nucleic acid in host cells. A typical expression cassette thus contains a promoter operably linked to the nucleic acid sequence encoding ribonuclease and signals required for efficient polyadenylation of the transcript, ribosome binding sites, and translation termination. Depending on the expression system, the nucleic acid sequence encoding ribonuclease may be linked to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET15b, pET23D, and fusion expression systems such as GST and LacZ. Epitope tags can also be added to recombinant proteins to provide convenient methods of isolation, e.g., 6-his.

For example, the cDNA of the RNAses of this invention were inserted into pET11d and the pET15b vectors. These vectors comprise, in addition to the expression cassette containing the coding sequence, the T7 promoter, transcription initiator and terminator, the pBR322 ori site, a bla coding sequence and a lac1 operator.

The vectors comprising the nucleic acid sequences encoding the RNAse molecules or the fusion proteins may be expressed in a variety of host cells, including *E. coli*, other bacterial hosts, yeast, and various higher eukaryotic cells such as the COS, CHO and HeLa cells lines and myeloma cell lines. In addition to cells, vectors may be expressed by transgenic animals, preferably sheep, goats and cattle. Typically, in this expression system, the recombinant protein is expressed in the transgenic animal's milk.

The recombinant nucleic acid will be operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The expression vectors or plasmids of the invention can be transferred into the chosen host cell by well-known methods such as calcium chloride transformation for *E. coli* and calcium phosphate treatment, liposomal fusion or electroporation for mammalian cells. Cells transformed by the plasmids can be selected by resistance to antibiotics conferred by genes contained on the plasmids, such as the amp, gpt, neo and hyg genes.

Once expressed, the RNAse protein can be purified according to standard procedures of the art, including ammonium sulfate precipitation, column chromatography (including affinity chromatography), gel electrophoresis and the like (see, generally, R. Scopes, *Protein Purification*, Springer-Verlag, N.Y. (1982), Deutscher, *Methods in Enzymology Vol.* 182: *Guide to Protein Purification.*, Academic Press, Inc. N.Y. (1990)).

2. Cleaving the RNAse Protein

After translation in the host cell, the RNAse which comprises a signal peptide is cleaved within the bacterial periplasm. Thus, no further manipulation of the protein is required for activity. For proteins with an amino terminal methionine, if a N-terminal glutamine or pyroglutamic acid is desired, the protein is treated with a cleaving agent or a combination of cleaving agents to remove the methionine. By "cleaving the amino terminal methionine" is meant cleaving the amino terminal methionine or amino terminal peptide from the polypeptides of SEQ ID NO:6, 8, 9, 13, 17, 21, 22, 26 and conservative variants thereof. Thus, by "cleaving the amino terminal methionine", a polypeptide of SEQ ID NO:2, 4, 11, 15, 19, 24 or conservative variants thereof is generated, optionally linked via peptide bonds to additional residues at the carboxy or amino terminus.

The cleaving agent may be a proteolytic enzyme such as an exopeptidase or endopeptidase (collectively, "peptidase") or a chemical cleaving agent. Exopeptidases include aminopeptidase M (Pierce, Rockford, Ill.) which sequentially remove amino acids from the amino-terminus. Cleavage of the amino terminal methionine by exopeptidases may be controlled by modulating the enzyme concentration, temperature, or time under which the cleavage takes place. The resulting mixture may be purified for the desired protein by means well known to those of skill, for example, on the basis of length by electrophoresis. The chemical cleaving agent, cyanogen bromide, is conveniently employed to selectively cleave methionine residues.

The cleaving agent employed to cleave the amino terminal methionine will typically be chosen so as not to break a peptide bond within the polypeptide of SEQ ID NO:2 and 15 or conservative variants thereof. Alternatively, use of a particular cleaving agent may guide the choice of conservative substitutions of the conservative variants of the polypeptides of the present invention. For example, the sequence of the native protein of SEQ ID NO:2 contains a methionine at position 23. As shown in SEQ ID NO:4 and SEQ ID NO:8, this methionine was changed to a leucine to prevent cleavage of the RNAse polypeptide chain with a 1 methionine by CNBr. Similarly, the native protein of SEQ ID NO:15 contains 2 internal methionines, one at position 22 and the other at position 57. As shown in SEQ ID NO:19 and 21, these methionines corresponding to position 22 and 57 in SEQ ID NO:15 were changed to leucines to prevent cleavage of the polypeptide chain when the N-terminal methionine was cleaved from the remainder of the protein.

The polypeptides of this invention may be purified to substantial purity by standard techniques, including selective precipitation with such substances as ammonium sulfate; column chromatography, immunopurification methods, and others. See, for instance, R. Scopes, PROTEIN PURIFICATION: PRINCIPLES AND PRACTICE, Springer-Verlag: N.Y. (1982), U.S. Pat. No. 4,673,641, Ausubel, and Sambrook.

C. Purification of RNAse from Bacterial Cultures

In the case of secreted proteins, the RNAses of this invention can be isolated and purified from the broth in which the expressing bacteria have been grown without having to resort to the cell lysis methods detailed below.

1. Purification of Protein from Bacterial Periplasm

It is anticipated that RNAse expression from *E. coli* may be low and the protein is exported into the periplasm of the bacteria. The periplasmic fraction of the bacteria can be isolated by cold osmotic shock in addition to other methods known to skill in the art (see Ausubel, and Trayer, H. R. & Buckley, III, C. E., *J. Biol. Chem.* 245(18):4842 (1970)).

To isolate proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The proteins present in the supernatant can be separated from the host proteins by standard separation techniques well known to those of skill in the art.

2. Purification of Inclusion Bodies

When recombinant proteins are expressed by the transformed bacteria in large amounts, typically after promoter induction; but expression can be constitutive, the proteins may form insoluble aggregates.

Purification of aggregate proteins (hereinafter referred to as inclusion bodies) involves the extraction, separation and/or purification of inclusion bodies by disruption of bacterial cells, typically but not limited by, incubation in a buffer of about 100–150 μg/mL lysozyme and 0.1% Nonidet P40®, a non-ionic detergent. The cell suspension can be ground using a Polytron® grinder (Brinkman Instruments, Westbury, N.Y.). Alternatively, the cells can be sonicated on ice. Alternate methods of lysing bacteria are described in Ausubel and Sambrook and will be apparent to those of skill in the art.

The cell suspension is centrifuged and the pellet containing the inclusion bodies resuspended in buffer, e.g., 20 mM Tris-HCl (pH 7.2), 1 mM EDTA, 150 MM NaCl and 2% Triton-X 100®, a non-ionic detergent. It may be necessary to repeat the wash step to remove as much cellular debris as possible. The remaining pellet of inclusion bodies may be resuspended in an appropriate buffer (e.g. 20 mM sodium phosphate, pH 6.8, 150 mM NaCl). Other appropriate buffers will be apparent to those of skill in the art.

Following the washing step, the inclusion bodies are solubilized by the addition of a solvent that is both a strong hydrogen acceptor and a strong hydrogen donor (or a combination of solvents each having one of these properties); the proteins that formed the inclusion bodies may then be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein.

After solubilization, the protein can be separated from other bacterial proteins by standard separation techniques.

D. Standard Protein Separation Techniques

1. Solubility Fractionation

Often as an initial step and if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol is to add saturated ammonium sulfate to a protein solution so that the resultant ammonium sulfate concentration is between 20–30%. This will precipitate the most hydrophobic of proteins. The precipitate is discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

2. Size Differential Filtration

If the size of the protein of interest is known or can be estimated from the cDNA sequence, proteins of greater and lesser size can be removed by ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

3. Column Chromatography

Proteins can be separated on the basis of their size, net surface charge, hydrophobicity and affinity for ligands. In addition, antibodies raised against proteins can be conjugated to column matrices and the proteins immunopurified. All of these methods are well known in the art.

It will be apparent to one of skill that chromatographic techniques can be performed at any scale and using equipment from many different manufacturers (e.g., Pharmacia Biotech).

In a preferred embodiment of this invention, the proteins are expressed from E. coli with a six histidine residue tag joined via a peptide bond to a 7 methionine. After the protein is purified to homogeneity as in Newton, et al., *Biochemistry* 35:545 (1996), the protein is cleaved at the 7 methionine as described above. The CNBr is removed and the mixture applied to a $Ni^{2+}$-NTA agarose column. The flow-through material is the cleaved product of interest.

E. Cyclization

Upon cleavage of the N-terminal methionine and other residues of the amino terminal peptide, a protein comprising the polypeptide of SEQ ID NO:2 or 15 or a conservatively modified variant thereof is generated. The glutamine residue of SEQ ID NO:2 or 15 is caused to cyclize by any number of means, including spontaneously or by catalysis, to a pyroglutamyl residue. Spontaneous hydrolysis of amino terminal glutamine residues to their pyroglutamyl form is well known to the skilled artisan and its rate may be hastened by, for example, increasing the temperature. See, e.g., Robinson, et al., *J. Am. Chem. Soc.* 95:8156–8159 (1973). Cytotoxicity or anti-viral activity of the resultant RNAse protein may be assessed by means herein disclosed and well known to the skilled artisan.

VII. Ligand Binding Moieties

The polypeptides and proteins of the present invention may also be joined via covalent or non-covalent bond to a ligand binding moiety. The RNAse molecule may be joined at the amino or carboxy terminus to the ligand or may also be joined at an internal region as long as the attachment does not interfere with the respective activities of the molecules. Immunoglobulins or binding fragments thereof (e.g., single-chain Fv fragments) may conveniently be joined to the polypeptides of the present invention. Vaughan, et al., *Nature Biotechnology* 14:309–314 (1996).

A. Chemically Conjugated Fusion Proteins

In one embodiment, the RNAse molecule is chemically conjugated to another molecule (e.g. a cytotoxin, a label, a ligand, or a drug or liposome). Means of chemically conjugating molecules are well-known to those of skill.

The procedure for attaching an agent to an antibody or other polypeptide targeting molecule will vary according to the chemical structure of the agent. Polypeptides typically contain a variety of functional groups; e.g. carboxylic acid (COOH) or free amine ($-NH_2$) groups, which are available for reaction with a suitable functional group on an RNAse molecule to bind the other molecule thereto.

Alternatively, the ligand and/or RNAse molecule may be derivatized to expose or attach additional reactive functional groups. The derivatization may involve attachment of any of a number of linker molecules such as those available from Pierce Chemical Company, Rockford Ill.

A "linker", as used herein, is a molecule that is used to join two molecules. The linker is capable of forming covalent bonds to both molecules. Suitable linkers are well known to those of skill in the art and include, but are not limited to, straight or branched-chain carbon linkers, heterocyclic carbon linkers, or peptide linkers. Where both molecules are polypeptides, the linkers may be joined to the constituent amino acids through their side groups (e.g., through a disulfide linkage to cysteine). However, in a preferred embodiment, the linkers will be joined to the alpha carbon amino and carboxyl groups of the terminal amino acids.

A bifunctional linker having one functional group reactive with a group on a particular agent, and another group reactive with an antibody, may be used to form a desired immunoconjugate. Alternatively, derivatization may involve chemical treatment of the ligand, e.g., glycol cleavage of the sugar moiety of a glycoprotein antibody with periodate to generate free aldehyde groups. The free aldehyde groups on the antibody may be reacted with free amine or hydrazine groups on an agent to bind the agent thereto. (See U.S. Pat. No. 4,671,958). Procedures for generation of free sulfhydryl groups on polypeptides, such as antibodies or antibody fragments, are also known (See U.S. Pat. No. 4,659,839).

Many procedure and linker molecules for attachment of various compounds including radionuclide metal chelates, toxins and drugs to proteins such as antibodies are known.

See, for example, European Patent Application No. 188,256; U.S. Pat. Nos. 4,671,958, 4,659,839, 4,414,148, 4,699,784; 4,680,338; 4,569,789; and 4,589,071; and Borlinghaus, et al. *Cancer Res.* 47:4071–4075 (1987) which are incorporated herein by reference. In particular, production of various immunotoxins is well-known within the art and can be found, for example in "Monoclonal Antibody-Toxin Conjugates: Aiming the Magic Bullet," Thorpe, et al., MONOCLONAL ANTIBODIES IN CLINICAL MEDICINE, Academic Press, pp. 168–190 (1982), Waldmann, *Science* 252:1657 (1991), U.S. Pat. Nos. 4,545,985 and 4,894,443.

In some circumstances, it is desirable to free the RNAse from the ligand when the chimeric molecule has reached its target site. Therefore, chimeric conjugates comprising linkages which are cleavable in the vicinity of the target site may be used when the effector is to be released at the target site. Cleaving of the linkage to release the agent from the ligand may be prompted by enzymatic activity or conditions to which the immunoconjugate is subjected either inside the target cell or in the vicinity of the target site. When the target site is a tumor, a linker which is cleavable under conditions present at the tumor site (e.g. when exposed to tumor-associated enzymes or acidic pH) may be used.

A number of different cleavable linkers are known to those of skill in the art. See U.S. Pat. Nos. 4,618,492; 4,542,225, and 4,625,014. The mechanisms for release of an agent from these linker groups include, for example, irradiation of a photolabile bond and acid-catalyzed hydrolysis. U.S. Pat. No. 4,671,958, for example, includes a description of immunoconjugates comprising linkers which are cleaved at the target site in vivo by the proteolytic enzymes of the patient's complement system. In view of the large number of methods that have been reported for attaching a variety of radiodiagnostic compounds, radiotherapeutic compounds, drugs, toxins, and other agents to antibodies one skilled in the art will be able to determine a suitable method for attaching a given agent to an antibody or other polypeptide.

B. Recombinant Fusion Proteins

In a preferred embodiment, the chimeric fusion proteins of the present invention are synthesized using recombinant DNA methodology. Generally this involves creating a DNA sequence that encodes the fusion protein, placing the DNA in an expression cassette under the control of a particular promoter, expressing the protein in a host, isolating the expressed protein and, if required, renaturing the protein.

In one embodiment, the ribonucleases of the invention are fused in frame to single chain antibodies. For tumor cell killing, the antibodies typically specifically bind to a target on the tumor cell. In other embodiment, the fusion proteins comprise a ligand which binds to a receptor on a tumor cell. For example, hCG binds and is cytotoxic to Kaposi's Sarcoma cells. By making a fusion protein comprising hCG and the ribonucleases of this invention, a compound that binds to the tumor cells and is more cytotoxic than hCG alone can be achieved.

DNA encoding the fusion proteins of this invention, as well as the recombinant RNAse molecules themselves, may be prepared by any suitable method, including, for example, cloning and restriction of appropriate sequences or direct chemical synthesis by methods such as the phosphotriester method of Narang, et al. *Meth. Enzymol.* 68:90–99 (1979); the phosphodiester method of Brown, et al., *Meth. Enzymol.* 68:109–151 (1979); the diethylphosphoramidite method of Beaucage, et al., *Tetra. Lett.* 22:1859–1862 (1981); and the solid support method of U.S. Pat. No. 4,458,066.

In a preferred embodiment, DNA encoding fusion proteins or recombinant RNAse proteins of the present invention may be cloned using DNA amplification methods such as polymerase chain reaction (PCR). If two molecules are joined together, one of skill will appreciate that the molecules may be separated by a peptide spacer consisting of one or more amino acids. Generally the spacer will have no specific biological activity other than to join the proteins or to preserve some minimum distance or other spatial relationship between them. However, the constituent amino acids of the spacer may be selected to influence some property of the molecule such as the folding, net charge, or hydrophobicity.

The nucleic acid sequences encoding the recombinant RNAse molecules or the fusion proteins may be expressed in a variety of host cells, including *E. coli*, other bacterial hosts, yeast, and various higher eukaryotic cells such as the COS, CHO and HeLa cell lines and myeloma cell lines. The recombinant protein gene will be operably linked to appropriate expression control sequences for each host. For *E. coli*, this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may also include splice donor and acceptor sequences.

The expression vectors or plasmids of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant RNAse or fusion proteins can be purified according to standard procedures of the art, as described above, including ammonium sulfate precipitation, affinity columns, column chromatography, gel electrophoresis and the like (see, generally, R. SCOPES, PROTEIN PURIFICATION, Springer-Verlag, N.Y. (1982), Deutscher, METHODS IN ENZYMOLOGY VOL. 182: *Guide to Protein Purification*., Academic Press, Inc. N.Y. (1990)). Substantially pure compositions of at least about 90 to 95% homogeneity are preferred, and 98 to 99% or more homogeneity are most preferred for pharmaceutical uses. Once purified, partially or to homogeneity as desired, the polypeptides may then be used therapeutically.

VIII. Uses of RNAse

The molecules of this invention, both the fusion proteins and RNAse alone can be used for a variety of uses.

A. Anti-Tumor Drug

The RNAse molecules are uniquely adapted for gene therapy applications. They can be fused to other therapeutic agents, for example, they could be fused to an anti-B cell lymphoma antibody, an anti-transferrin receptor antibody or an anti-colon cancer antibody. As mentioned above, native ONCONASE® has anti-tumor effects in vivo and preferentially kills rapidly dividing cells stimulated by serum or growth promoting agents such as ras. The RNAses of this invention can be used in a similar manner. The RNAses of this invention are readily internalized in the cell. Their activity can be further facilitated by joining them to a nuclear localization signal (NLS) and the like to redirect the molecules within the cell. Of particular use in tumor cells would be to target telomerase, an enzyme subject to degradation by ribonuclease.

Telomerase is being investigated as a "universal cancer target." It is an RNA protein that is located in the nucleus. It has been shown that antisense to telomerase RNA can inhibit the function of the enzyme and block the growth of cancer cells (Feng, et al., *Science* 269:1236 (1995)). Previous studies have shown RNase can destroy the activity of the enzyme when incubated with a cell extract containing telomerase. Thus a RNAse molecule can be made, which when administered to a person with cancer, would be routed to the nucleus of cells.

In a gene therapy protocol, a vector containing an expression cassette which encodes for the RNAses of this invention can be used either to infect cells ex vivo, for example hematopoietic cells in lymphoma or leukemia, or to infect cells in vitro. Recently, there has been a lot of activity in synthesizing retroviral vectors with chimeric coat proteins. The chimeric proteins typically comprise two domains, one of which is embedded in the viral coat and is of retroviral origin. The second domain is heterologous to the virus and is a member of a binding pair. For example, the second domain consists of a single chain Fv fragment which binds to a tumor cell surface marker or it is the ligand to which an antibody expressed on the cell surface binds. Other binding pairs, not necessarily monoclonal antibodies and their ligands will be apparent to those of skill.

Studies with ONCONASE® have indicated other potential uses. It has been found that ONCONASE® synergizes with ras in microinjection studies. Onconace® does not synergize with ras when it enters the cell via its own routing but requires a CAAX motif to localize ras at the plasma membrane (C=Cys, A=an aliphatic amino acid, X=S,M,C,A, or Q, an example is Cys-Val-Ile-Met. Importantly this type of sequence has been shown to target heterologous proteins to the plasma membrane (Hancock, J., et al., *EMBO J.* 10:4033 (1991)). The RNAses of this invention have identical uses.

B. Targeted Fusion Proteins

The RNAses of this invention can be joined to a ligand binding moiety that is specific for tumor cells. Examples of such ligand binding moieties include, but are not limited to, monoclonal antibodies directed against tumor cell markers such as heregulin, CD22, PSA, etc.; cytokines that target tumor cells, such as tunor necrosis factor; and other tumor cell binding proteins, including hCG.

In addition, one of skill will recognize that two cytotoxic factors can be joined to one ligand binding moiety, For example, the RNAses of this invention can be joined to a monoclonal antibody directed against a tumor cell marker which is also joined to a synthetic drug with cytotoxic activity, such as paclitaxel or methotrexate.

Finally, the fusion proteins of this invention find use as cytotoxic agents against cells other than tumor cells. For example, the RNAses of this invention are joined to ligand binding moieties that specifically target B cells which secrete antibodies directed against self. Thus, the RNAses of this invention are useful in the treatment of autoimmune diseases.

IX. Pharmaceutical Compositions

The molecules and fusion proteins employing them of this invention are useful for parenteral, topical, oral, or local administration, such as by aerosol or transdermally, for prophylactic and/or therapeutic treatment. The pharmaceutical compositions can be administered in a variety of unit dosage forms depending upon the method of administration. For example, unit dosage forms suitable for oral administration include powder, tablets, pills, capsules and lozenges. It is recognized that the subject molecules and fusion proteins and pharmaceutical compositions of this invention, when administered orally, must be protected from digestion. This is typically accomplished either by complexing the protein with a composition to render it resistant to acidic and enzymatic hydrolysis or by packaging the protein in an appropriately resistant carrier such as a liposome. Means of protecting proteins from digestion are well known in the art.

The pharmaceutical compositions of this invention are particularly useful for parenteral administration, such as intravenous administration or administration into a body cavity or lumen of an organ. The compositions for administration will commonly comprise a solution of the chimeric molecule dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of therapeutic molecule in these formulations can vary widely, and will be selected primarily based on fluid volumes, viscosities, body weight and the like in accordance with the particular mode of administration selected and the patient's needs.

Thus, a typical pharmaceutical composition for intravenous administration would be about 0.1 mg to 10 mg per patient per day. Dosages from 0.1 mg up to about 100 mg per patient per day may be used, particularly when the drug is administered to a secluded site and not into the blood stream, such as into a body cavity or into a lumen of an organ. Actual methods for preparing parenterally administrable compositions will be known or apparent to those skilled in the art and are described in more detail in such publications as REMINGTON'S PHARMACEUTICAL SCIENCE, 15th ed., Mack Publishing Company, Easton, Pa. (1980).

The compositions containing the present recombinant RNAse molecules or the fusion proteins or a cocktail thereof (i.e., with other proteins) can be administered for therapeutic treatments. In therapeutic applications, compositions are administered to a patient suffering from a disease, in a cytotoxic amount, an amount sufficient to kill cells of interest. An amount adequate to accomplish this is defined as a "therapeutically effective dose." Amounts effective for this use will depend upon the severity of the disease and the general state of the patient's health.

Single or multiple administrations of the compositions may be administered depending on the dosage and frequency as required and tolerated by the patient. In any event, the composition should provide a sufficient quantity of the proteins of this invention to effectively treat the patient.

Although the present invention has been described in some detail by way of illustration and example for purposes of clarity of understanding, it will be obvious that certain changes and modifications may be practiced within the scope of the appended claims.

X. EXAMPLES

A. Example 1

Expression Pattern of RNAse in *Rana pipiens* Tissues

A DNA sequence corresponding to amino acid residues 16–98 of ONCONASE® was cloned by PCR amplification of *Rana pipiens* genomic DNA and sequenced. The sequence, consisting of 252 bp of DNA encoding the ribonuclease was designated *Rana* clone 9. Total cellular RNA was isolated from either male or female *Rana pipiens* tissues using RNA STAT-60 (TEL-TEST "B", Inc.) according to the manufacturer's protocol. Poly A+ containing mRNA was prepared using an Oligotex mRNA kit (Qiagen). Poly (A+) RNA was size fractionated on a 1% agarose gel containing 6% formaldehyde and blotted onto Nitran® nylon membranes (Schleicher & Schuell) in 10×SSC overnight. The membrane was rinsed in 2×SSC for 5 min, air dried and the RNA was cross linked to the membrane by exposure to UV light (Ultra-Lum) for 2 min. The RNA blot was hybridized at 42° C. for 16–18 hours with a [$^{32}$P]-labeled DNA probe prepared from 30 ng of *Rana* clone 9 insert using the oligo labeling kit from Amersham. After hybridization, the RNA blot was washed twice in 1×SSC, 1% SDS for 20 min at 42° C. The blot was exposed to X-ray film for 4 days. The molecular size of mRNA was estimated using 0.24–9.5 kb RNA molecular weight markers (BRL).

Since ONCONASE® is isolated in large quantities from the oocytes of *Rana pipiens*, it was assumed that high levels of RNAse RNA would be present in the mRNA from oocytes. Surprisingly, mRNA reacting with *Rana* clone 9 was not detected in *Rana pipiens* oocyte, heart, lung and kidney tissues. The only mRNA signal detected with *Rana* clone 9 was a strongly hybridizing 3.6 kb RNA in mRNA isolated from *Rana pipiens* liver. As a protocol control, the same northern blot was probed with a [$^{32}$p]-labeled human actin cDNA. Actin mRNA was detectable in all of the tissues. In another northern analysis with four-fold more liver poly (A+) mRNA, a second weakly hybridizing mRNA of about 950 bp was detected.

To confirm that RNAse mRNA was present in *Rana pipiens* liver but not in oocytes, RT-PCR was performed using total RNA isolated from *Rana pipiens* liver and oocytes and with the degenerate primers used in the cloning of the *Rana* clone 9 insert.

Total RNA was isolated from *Rana pipiens* liver and oocytes. The procedure of Chen, et al., *Oncogene* 12:741 (1996) was used. Briefly, PCR was carried out under the following conditions: 94° C. for 5 minutes and then 30 cycles of denaturation at 94° C. for 1 min, annealing for 2 min at 55° C., and primer extension for 1 min at 72° C. The degenerate forward primer used [(5'-AG(GA)GATGT(GT)GATTG(TC)GATAA(CT)ATCATG-3' (SEQ ID NO:30)] with the reverse degenerate primer [5'-AAA(GA)TG(CA)AC(AT)GG(TG)GCCTG(GA)TT(CT)TCACA-3' (SEQ ID NO:31)].

The PCR products were analyzed on a 1.5% agarose gel and stained with ethidium bromide. the PCR product obtained from liver was subcloned into PCR3 vector by TA cloning (Ivitrogen) and sequenced.

A band of the expected size of about 250 bp was generated in the liver RNA but not oocyte RNA, consistent with the result from northern blot analysis. To ensure that the 250 bp band represented RNAse cDNA, this PCR product was subcloned and its DNA sequence determined with the Sequenase v. 2.0 kit (United States Biochemical).

Bases 1, 7, 13, 23 and 235 of the PCR product differed from the sequence of *Rana* clone 9. With the exception of the change at base 23, all of the other base changes were within the degenerate primer sequences. The difference at base 23 is an A to T transition which results in conservative amino acid change from threonine to serine, and could be due to polymorphism of the RNAse gene or a PCR error.

B. Example 2

Expression of RNAse in *Rana pipiens*

To determine if RNAse is present in *Rana pipiens* oocytes or other tissues, protein extracts were isolated from various *Rana pipiens* tissues and separated on a 4–20% Tris-Glycine SDS-containing polyacrylamide gel. The protein extracts were transferred to a nitrocellulose membrane using 1× transfer buffer (Novagen) at 250 mA for 45 min. The membrane was probed with primary and secondary antibodies as described in Chen, et al., *Oncogene* 12:241 (1996). The primary anti-ONCONASE® antibody was used at 1:100 dilution. The detecting antibody (horseradish peroxidase labeled donkey anti-rabbit Ig (Amersham)) was used at 1:2500 dilution. The antibodies were visualized using an ECL detection kit from Amersham.

The western blot analysis demonstrated that a protein of the correct size (12 kDa) was present in extracts from oocytes. Other tissues, including liver, did not contain a 12 kDa protein that reacted with the anti-ONCONASE® antibody. High molecular weight bands were also observed. These represented other forms of ONCONASE® (e.g. glycosylated or multimeric) or represented related members of the pancreatic ribonuclease A amphibian superfamily. It had been previously determined that the anti-ONCONASE® antibody cross reacts with other pancreatic type RNAses such as bovine pancreatic ribonuclease as well as two human RNAses; eosinophil-derived neurotoxin and angiogenin.

C. Example 3

Isolation and Cloning of cDNA from *Rana pipiens* Liver mRNA

Liver poly (A+) RNA was purified twice using the poly (A+) Pure kit (Ambion). The cDNA library was constructed using a ZAP-cDNA synthesis kit and Gigapack II gold packaging extracts according to the manufacturer's protocol (Stratagene). The library contained about 1.5×10$^6$ pfu from 5 µg of liver poly (A+) RNA and was amplified once according to Stratagene's protocol. The library titer after amplification was 9×10$^9$ pfu/mL. About 3×10$^5$ plaques were screened by using a [$^{32}$P]-labeled insert of *Rana* clone 9 following Stratagene's procedure. Positive clones (3a1b, 4a1b and 5a1b) were excised from the lambda ZAP II vector and subeloned into pBluescript SF-vector. Plasmid DNA was prepared using the Qiagen spin plasmid miniprep kit.

Clone 5a1b was digested with KpnI and HindIII to generate 3' and 5' protruding ends, and digested with exonuclease III to generate 5a1b deletion clones. Overlapping deletions were generated according to the manufacturer's instructions with the Erase-a-Base system (Promega). The size of DNA inserts from the deletion clones were estimated from agarose gel analysis, and the selected clones were sequenced using the T7 promoter primer. The cDNA of clone 4a1b, the 5' end of clone 3a1b and part of the clone 5a1b were sequenced using T3, T7 and appropriate primers. All the sequencing reactions were performed using the Sequenase v. 2.0 kit (United States Biochemical) and α-[35S] dATP (>1000 Ci/mmole, Amersham). Both strands of clone 5a1b were sequenced.

Clone 5a1b cDNA (SEQ ID NO:27) which was about 2.8 kb in size, contained an open reading frame (ORF) at the 5' end. The deduced amino acids at positions 1–23 were characteristic of a signal peptide with a charged amino acid within the first 5 amino acids, a stretch of at least 9 hydrophobic amino acids to span the membrane, and a applied to a CM Sephadex C-50 column. Final purification to homogeneity as assessed by gel electrophoresis was achieved by size exclusion chromatography.

E. Example 5

The following oligonucleotides were synthesized:

Assembly of Synthetic RaCOR1 Gene

```
The following oligonucleotides were synthesized:

5'-CAGAACTGGGCTACTTTCCAGFCAGAAACATATCATCAACACTCCGATCATCT       (SEQ ID NO:32)
G CAACACTATCATGGACAACAACATCTACATCGTTGGTGGTCAG-3'

5'-TACATCGTTGGTGGTCAGTGCAAACGTGTTAACACTTTCATCATCTCTCTGCTA      (SEQ ID NO:33)
CTACTGTTAAACGTATCTGCACTGGTGTTATC-3

5'-ATCTGCAGTGGTGTTACTAACATGAACGTTCTGTCTACTACTCGTTTCCAGCTG      (SEQ ID NO:34)
AACACTTGCACTCGTACTTCTATCACTCCGCGTCCGTGCCCG-3

5'-GTTGATAACACCAGTGCAGAT-3'                                    (SEQ ID NO:35)

5'-ATCTGCACTGGTGTTATCAAC-3'                                    (SEQ ID NO:36)

5'-ACTCCGCGTCCGTGCCCGTACTCTTCTCGTACTGAAACTAACTACATCTGCGTT      (SEQ ID NO:37)
AAATGCGAAAACCAGTACCCGGTTCATTTCGCTGGTATCGG-3'

5'-ATATATCTAGAAATAATTFfATTTAACTTTAAGAAGGAGATATACATATGCAG       (SEQ ID NO:38)
A ACTGGGCTAGTTTCCAG-3'

5'-CGCGCCGGATCCCTACTACGGGCAACGACCGATACCAGCGAAATGAAC-3'         (SEQ ID NO:39)

5'-CAGAACTGGGCTACTTTCCAGCAGAAACATATCATCAACACTCCGATCATCTG       (SEQ ID NO:40)
CAACAGTATCCTGCAGAACAACATCTACATCGTTGGTGGTCAG-3'

5'-ATCTGCACTGGTGTTATCAACCTGAACGTTCTGTCTACTACTCGTTTCCAGCTG      (SEQ ID NO:41)
AACACTTGCACTCGTACTTCTATCACTCCGCGTCCGTGCCCG-3'
``` cysteine at position 23. The putative signal peptide sequence was followed by a highly conserved but not identical amino acid sequence compared to ONCONASE®. There were four amino acid differences between the ORF of clone 5a1b and ONCONASE® including amino acid residues 11, 20, 85 and 103. With the exception of a conservative change at amino acid residue 11, all the other amino acid conversions are between polar and charged amino acid residues.

D. Example 4

Cloning and Expression of RaPLR1

Oligonucleotide primers were designed to clone the cDNA sequence of *Rana pipiens* liver RNAse (RaPLR1) as a [met-1] fusion protein as well as to modify the primary amino acid structure by changing the N-terminal amino acid residue following the initiating methionine from glutamine to serine ([Met-(-1)]RaPLR1(Q1S). Thus, the recombinant RNAses obtained from the bacteria in this expression system contain an extra methionine at the amino terminal end [Met-(-1)].

Amplification of these sequences was carried out in a thermal cycler and the DNA was cloned into an expression vector using methodology previously described in Newton, et al., The plasmids were expressed in B121(DE3) *E. coli* and the recombinant proteins were isolated from inclusion bodies as described (Newton, et al., supra) before being PCR reactions were performed containing:
1×reaction buffer (100 mM Tris-HCl, pH 8.3, 500 mM KCl, 1.5 mM MgCl$_2$);
0.4 mM nucleotides;
5.0 units Amplitaq® DNA polymerase;
0.5 μM oligonucleotides (SEQ ID NO:32–41) in the combinations listed below; and water to adjust to 100 μL final volume.

The thermal cycler conditions were as follows: 94° C. for 5 min preincubation then 20 cycles at 94° C. for 1 min; 55° for 2 min; and 72° C. for 2 min. The first PCR reaction contained SEQ ID NO:32, 33 and 35, which comprised the 5' half of the RNAse gene. The second PCR reaction contained SEQ ID NO:34, 36, and 37 which comprised the 3' half of the gene. For the proteins wherein positions corresponding to positions 22 and 57 of SEQ ID NO:15 were changed to leucines, the first reaction was with SEQ ID NO:33, 35 and 38 to synthesize the 5' half of the gene and the second was with SEQ ID NO:36, 37 and 38 to synthesize the 3' half of the gene.

The PCR products were purified using the Geneclean® II kit from Bio 101, Inc. Vista, Calif.) according to the manufacturer's instructions. The following PCR reactions were performed under conditions as above to assemble the complete gene as shown in FIG. 1. To assemble the non-mutated gene, SEQ ID NO:38 and 39 were added to the purified PCR products. To assemble the gene with the methionine to leucine mutation, SEQ ID NO:40 and 41 were used.

The assembled genes were purified by the GeneClean® procedure, cleaved with the endonucleases XbaI and BamHI overnight and ligated into the pET-11d vector. The DNA was sequences, expressed and the protein purified as described in Newton, et al., *Biochemistry* 35:545 (1996). The nucleotide sequence of the non-mutated synthetic gene is shown in SEQ ID NO:14. The amino acid sequence of the gene product is as shown in SEQ ID NO:15.

The clone containing the mutations was subsequently modified by PCR to insert an NdeI restriction site for ligation into the pET-15b vector (which encodes a six histidine tag as well as a thrombin cleavage site at the 5' end of the expression cassette insertion point) by using primers as shown in SEQ ID NO:39 and 5'-GGATTCCATATGCAGAACTGGGCTATTTTCCAG-3' (SEQ ID NO:42). The PCR methods were as shown above.

F. Example 6

Purification of RNAse with Mutations

The purified *Rana catesbeiana* proteins of Example 5 contained a six histidine tail at the N-terminus. The protein was treated with CNBr as described by Gross & Witkop, *J. Biol. Chem.* 237:1856 (1962). In brief, the protein (dissolved in 0.1 N HCl) was treated with 100-fold molar excess of CNBr for 24 hours at ambient temperature. CNBr cleaves on the carboxyl side of methionine residues; the mutated protein contains only one methionine at the 1 position. The CNBr was removed by lyophilization and the protein dissolved in 0.1 M Tris-HCl, pH 7.5. The soluble protein was applied to a $Ni^{2+}$-NTA agarose column (Qiagen) to remove the uncleaved protein from the +1 Gln cleaved protein. The His tail bound to the $Ni^{2+}$-NTA column and the cleaved RNAse was found in the flow-through. Elution of the column yielded the His-containing cleavage product and non-cleaved $(His)_6$ (SEQ ID NO:43) containing protein. Densitometry analysis of cleaved and non-cleaved protein demonstrated that 50% of the protein was cleaved by CNBr.

The mutated protein was allowed to cyclize at the N-terminus to form pyroglutamic acid by dialysis in 0.2 M $KPO_4$ buffer. An amino end group analysis was performed to ensure the presence of a blocked $NH_2$-terminus.

G. Example 7

Analysis of RNAse Activity

The methods used to assay the recombinant RNAses of this invention were done as described in Newton, et al., *Protein Engineering* 10:463 (1997). Briefly, ribonuclease activity using high molecular weight RNA and tRNA was determined at 37° C. by monitoring the formation of perchloric acid-soluble nucleotides. The buffer was 0.16 M Tris-HCl, pH 7.5 with 1.6 mM EDTA and 0.2 mg/mL human serum albumin (HSA). Ribonuclease activity was assayed according to DePrisco, et al., *Biochemica et Biophysica Acta* 788:356 (1984) and Libonati & Floridi, *Eur. J. Biochem.* 8:81 (1969) by measuring the increase with time in absorbance at 260 nm. Incubation mixtures (1 mL of 10 mM imidazole, 0.1 M NaCl, pH 7.0) contained substrate and appropriate amounts of enzyme solution at 25° C. Final substrate concentration in the assays was 0.33 mg/mL tRNA. Each assay was repeated 2–6 times and the average value was used in data treatment. Kinetic parameters were obtained with the aid of the data analysis program of Cleland, *Methods of Enzymol.* 63:103 (1979).

The results of the assay is shown in Table I.

TABLE I

Ribonuclease Activity

| RNAse | RNAse Activity (units/mg protein) | Fold Increase |
|---|---|---|
| native ONCONASE ® | 9 | |
| recombinant *Rana catesbeiana* RNAse | 200 | 22 |
| recombinant ONCONASE ® (Q1S) | 1.5 | |
| recombinant *Rana pipiens* RNAse (Q1S) | 2.5 | 1.7 |

The cytotoxicity of the RNAses of this invention was determined by measuring the protein synthesis of tumor cells in the presence of the RNAse. Protein synthesis was measured as previously described in Rybak, et al., *J. Biol. Chem.* 266:21202 (1991). 0.1 mL of cells ($2.5 \times 10^4$ cells/mL) were plated into 96-well microtiter plates in Dulbecco's Minimum Essential Medium supplement with 10% heat-inactivated fetal bovine serum (Δ-FBS); additions were made in a total volume of 10 μL; and the plates were incubated at 37° C. for the times indicated. Phosphate-buffered saline (PBS) containing 0.1 mCi of $[^{14}C]$-leucine was added for 2–4 hours, and the cells were harvested onto glass fiber filters using a PHD cell harvester, washed with water, dried with ethanol and counted in a scintillation counter. The results are expressed in Table II as percent of $[^{14}C]$-leucine incorporation in the mock-treated wells.

Recombinant ONCONASE® with a methionine at the 1 position was not very cytotoxic since correct hydrogen bonding at the active site is fostered by the pyroglutamic acid N-terminus of the native protein (Newton, et al., *Protein Engineering* 10:463 (1997)). In the four human tumor cell lines tested, the recombinant *Rana pipiens* liver RNAses were more active than recombinant ONCONASE®. It appears that the four amino acid differences in RaPLR1 change the active site configuration such that is does not display the degree of dependence ONCONASE® has on the N-terminal pyroglutamic acid residue for correct hydrogen bonding at the active site.

Similarly, RaCOR1 was also more cytotoxic than recombinant ONCONASE®. Again, most likely this is due to an active site that is not dependent on the N-terminal pyroglutamic acid for correct hydrogen bonding.

TABLE II

Cytotoxicty in human tumor cells of recombinant RNAses (IC$_{50}$ (nM))

| Cell Line | Tumor type | rec ONCONASE ® | rec RaPLR1 | Fold Increase | rec RAPLR Q1S | Fold Increase | rec RACOR | Fold Increase |
|---|---|---|---|---|---|---|---|---|
| SF539 | Glioma | 29,200 | 2,300 | 13 | 417 | 70 | 1,300 | 22 |
| HS578T | Breast | >8,300 | 8,300 | >1 | 670 | >8 | 2,500 | >3 |
| ACHN | Kidney | 26,700 | 3,300 | 8 | 1,580 | 17 | 1,000 | 11 |
| Malame | Melanoma | 25,000 | 580 | 43 | 750 | 33 | 1,000 | 25 |
| MCF7 | Breast | >8,300 | | | | | 320 | 26 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed:

1. A cytotoxic reagent comprising a recombinant ribonuclease linked to an antibody directed against a cell surface antigen on a cancerous B cell, wherein the recombinant ribonuclease is expressed from recombinant DNA and has (a) measurable ribonuclease activity; (b) a glutamine or serine at position 1; (c) a leucine at position 11; an asparagine at position 21, a threonine at position 85, and a histidine at position 103, such positions being determined with reference to those specified amino acid positions of SEQ ID NO:2; and (d) at least 80% identity to SEQ ID NO:2.

2. The cytotoxic reagent of claim 1, wherein the antibody is directed against CD22.

3. A method of killing cancer cells comprising contacting cells to be killed with a cytotoxic reagent expressed by a recombinant DNA comprising a sequence selected from the group consisting of SEQ ID NO:2, SEQ ID NO:4, SEQ ID NO:6, SEQ ID NO:8, SEQ ID NO:11, SEQ ID NO:13, SEQ ID NO:15, SEQ ID NO:17, SEQ ID NO:19, SEQ ID NO:21, SEQ ID NO:24, and SEQ ID NO:26 covalently linked to an antibody directed against a cell surface antigen on a cancerous B cell.

4. The method of claim 3, wherein the antibody is directed against CD22.

5. The cytotoxic reagent of claim 1, wherein the antibody is a recombinant single chain antibody.

6. The cytotoxic reagent of claim 1, wherein the cytotoxic reagent is expressed from recombinant DNA.

7. The cytotoxic reagent of claim 2, wherein the antibody has a recombinant LL2 antigen binding fragment.

8. The method of claim 4, wherein the antibody has a recombinant LL2 antigen binding fragment.

* * * * *